US012751713B2

(12) United States Patent
Sauer

(10) Patent No.: US 12,751,713 B2
(45) Date of Patent: Oct. 6, 2026

(54) DEVICE FOR CARDIAC SURGERY AND METHODS THEREOF

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 0 days.

(21) Appl. No.: 18/241,510

(22) Filed: Sep. 1, 2023

(65) Prior Publication Data

US 2023/0404570 A1 Dec. 21, 2023

Related U.S. Application Data

(60) Continuation of application No. 17/072,125, filed on Oct. 16, 2020, now Pat. No. 11,771,417, which is a (Continued)

(51) Int. Cl.
*A61B 17/04* (2006.01)
*A61B 17/00* (2006.01)
(Continued)

(52) U.S. Cl.
CPC ...... *A61B 17/0482* (2013.01); *A61B 17/0218* (2013.01); *A61B 17/0469* (2013.01); (Continued)

(58) Field of Classification Search
CPC ........ A61B 17/06114; A61B 17/06119; A61B 17/0401; A61B 17/0218; A61B 17/08; (Continued)

(56) References Cited

U.S. PATENT DOCUMENTS 4,755,181 A 7/1988 Igoe
5,669,919 A 9/1997 Sanders et al.
5,891,160 A 4/1999 Williamson, IV et al.
(Continued)

FOREIGN PATENT DOCUMENTS

JP 2012-245095 12/2012
WO 95/15715 6/1995
WO 99/60929 12/1999

OTHER PUBLICATIONS

Extended European Search Report for U.S. Appl. No. 17/813,917, dated Oct. 1, 2019, 10 pages.
International Search Report and Written Opinion, for International Application No. PCT/US17/37203, filed Jun. 13, 2017, mailed Aug. 31, 2017, 52 pages.
(Continued)

*Primary Examiner* — Katherine M Shi
*Assistant Examiner* — Mohammed S Adam
(74) *Attorney, Agent, or Firm* — Michael E. Coyne

(57) ABSTRACT

A device for cardiac surgery includes a first frame member having a first end that is pivotably coupled to a first end of a second frame member, and two or more apertures are disposed through each of the first and second frame members that are each configured to receive a corresponding portion of suture. The first frame member and the second frame member are pivotably displaceable between a first position and a second position. In the first position, a second end of the first frame member and a second end of the second frame member are separated by a first distance, and in the second position, the second end of the first frame member and the second end of the second frame member are separated by a second distance that is greater than the first distance.

8 Claims, 16 Drawing Sheets

Related U.S. Application Data division of application No. 15/750,215, filed as application No. PCT/US2017/037203 on Jun. 13, 2017, now Pat. No. 11,026,675.

(60) Provisional application No. 62/350,949, filed on Jun. 16, 2016, provisional application No. 62/349,414, filed on Jun. 13, 2016.

(51) Int. Cl.
*A61B 17/02* (2006.01)
*A61B 17/06* (2006.01)

(52) U.S. Cl.
CPC ............... *A61B 2017/00243* (2013.01); *A61B 17/0206* (2013.01); *A61B 2017/0237* (2013.01); *A61B 17/06* (2013.01)

(58) Field of Classification Search
CPC ....... A61B 17/11; A61B 17/12; A61B 17/122; A61B 2017/0416; A61B 2017/00243; A61B 2017/0237; A61F 2/0063; A61F 6/20
See application file for complete search history.

(56) References Cited

U.S. PATENT DOCUMENTS

| | | | | |
|---|---|---|---|---|
| 6,063,021 | A * | 5/2000 | Hossain ............ | A61B 17/0218 600/37 |
| 7,758,500 | B2 | 7/2010 | Boyd et al. | |
| 8,057,538 | B2 | 11/2011 | Bergin et al. | |
| 8,142,495 | B2 | 3/2012 | Hasenkam et al. | |
| 8,388,525 | B2 | 3/2013 | Poo | |
| 2002/0065451 | A1 | 5/2002 | Spence et al. | |
| 2003/0176916 | A1 | 9/2003 | Ryan et al. | |
| 2004/0073241 | A1 | 4/2004 | Barry et al. | |
| 2005/0267572 | A1 | 12/2005 | Schoon et al. | |
| 2010/0179569 | A1 | 7/2010 | Salky | |
| 2011/0082538 | A1 | 4/2011 | Dahlgren et al. | |
| 2012/0165930 | A1 | 6/2012 | Gifford, III et al. | |
| 2015/0073537 | A1 | 3/2015 | Jimenez et al. | |
| 2017/0065266 | A1 | 3/2017 | Landanger | |

OTHER PUBLICATIONS

Product Literature, Geister, Performance needs space . . . Izzat Spring Retractor, Developed in cooperation with Professor M. Bashar Izzat, 2010, 2 pages.

Miami Instruments, Miami Method Tailor-Made Exposure Products, Aortic Root Exposure Device, 2017, 6 pages.

* cited by examiner

DEVICE FOR CARDIAC SURGERY AND METHODS THEREOF

RELATED APPLICATIONS

This application is a continuation of U.S. application Ser. No. 17/072,125, filed on Oct. 16, 2020, which is a divisional of and claims priority to U.S. 371 application Ser. No. 15/750,215, filed Feb. 5, 2018. The U.S. 371 application Ser. No. 15/750,215 claims priority to international application PCT/US2017/037203, filed Jun. 13, 2017, which claims priority to U.S. provisional patent application No. 62/349,414, filed Jun. 13, 2016, and U.S. provisional patent application No. 62/350,949, filed Jun. 16, 2016, the disclosure of each of which is hereby incorporated by reference in its entirety.

FIELD

The claimed invention relates to surgical devices, and more specifically to a device for cardiac surgery and methods thereof.

BACKGROUND

In many types of minimally invasive cardiac surgery, it is often desirable to access the aortic valve and/or left ventricle of the heart through a portion of the aorta. In order to create an aortotomy (incision through the aorta), it is first necessary to securely clamp and/or occlude the aorta away from the heart, place the patient on bypass perfusion, and temporarily stop the heart from beating, for example, with cardioplegia. This depressurizes the aorta and can cause the walls of the aorta to flop down after an incision is made in the aorta, thereby blocking the surgeon's view of the aortic valve through the incision. Furthermore, even when the flaps of the aorta around the incision are held out of the way, it can still be difficult to see the aortic root where the flaps of the aortic valve are attached to the heart. Therefore, it would be helpful if there were a device for cardiac surgery which could help to increase a surgeon's visualization of the aortic root in such a minimally invasive surgical procedure.

SUMMARY

A device for cardiac surgery is disclosed. The device has a frame and a plurality of suture guides spaced about the frame.

A further device for cardiac surgery is disclosed. The device has a plurality of pairs of suture guides spaced about the frame. The device also has a plurality of suture tubes, with one suture tube corresponding to each pair of suture guides. The device further has a plurality of snares, each corresponding to and passed through one of the plurality of suture tubes so that a handle at one end of the snare protrudes from a proximal end of the corresponding suture tube and a snare loop at another end of the snare protrudes through a distal end of the corresponding suture tube, and wherein the snare loop further protrudes through one of the suture guides in the corresponding pair of suture guides. The device also has a plurality of sutures, each corresponding to one of the pairs of suture guides and coupled to the suture guide in the corresponding pair of suture guides which does not have the snare loop passing through it.

Another device for cardiac surgery is disclosed. The device has a frame and a plurality of suture guides spaced about the frame. The device also has a plurality of legs extending downward from the frame, each leg coupled to a foot. The device further has a plurality of sinus supports coupled to the frame.

Figure 1:
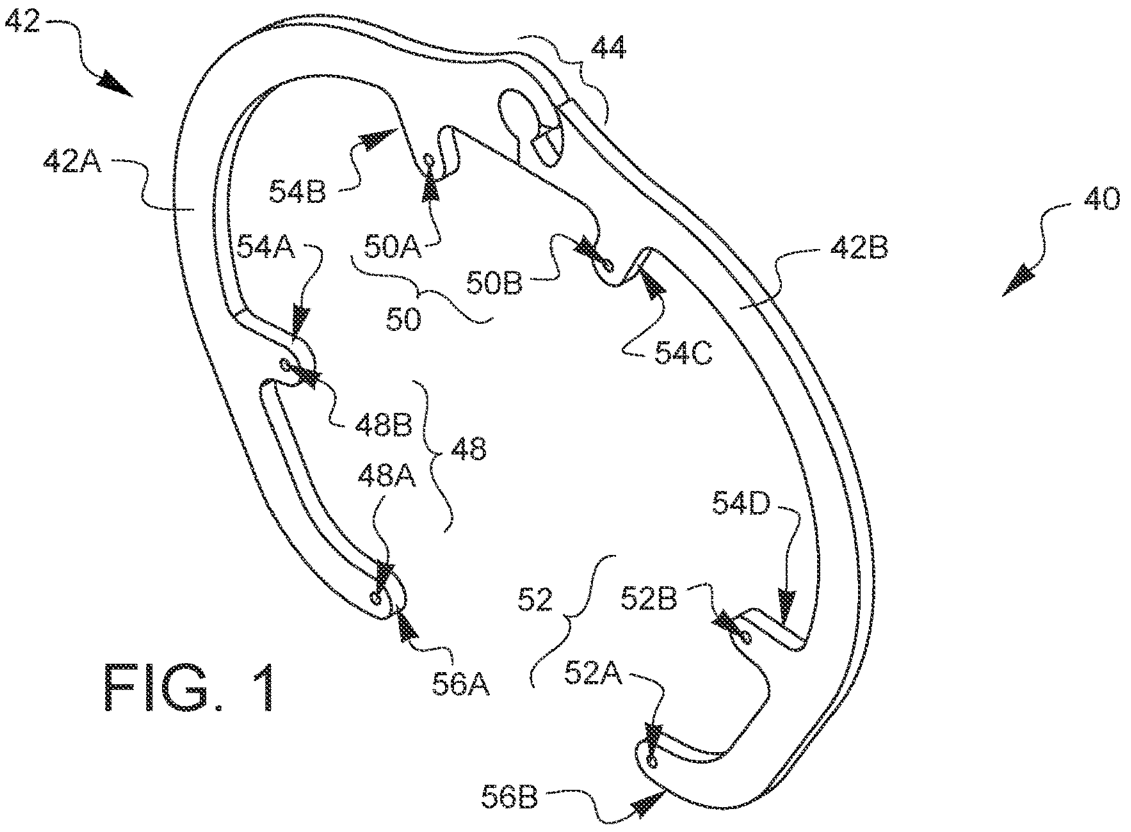
FIG. 1 is a perspective view of one embodiment of a device for cardiac surgery.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

Figure 2:
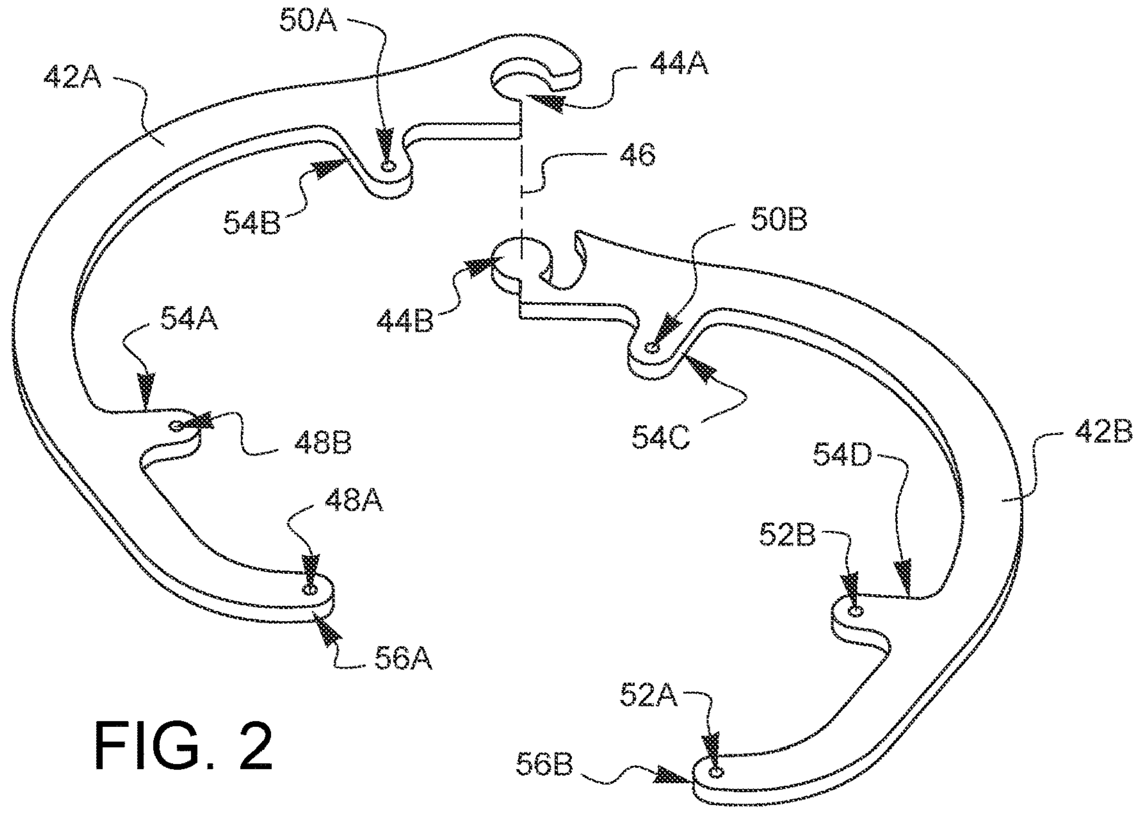
FIG. 2 is an exploded view of the device for cardiac surgery from FIG. 1.

FIG. 1 is a perspective view of one embodiment of a device 40 for cardiac surgery. FIG. 2 is an exploded view of the device 40 for cardiac surgery from FIG. 1. The device 40 has a frame 42 which comprises first and second frame parts 42A, 42B. The first and second frame parts 42A, 42B are pivotably coupled together by a hinge 44 formed from corresponding first and second hinge features 44A, 44B. The corresponding hinge features 44A, 44B can be held together, while still allowing rotation about a pivot axis 46, by using a variety of techniques known to those skilled in the art. In this embodiment, the hinge 44 is made from portions of the first and second frame parts 42A, 42B. In other embodiments, a hinge could be a separate part which is coupled between the frame parts 42A, 42B.

The device 40 for cardiac surgery also has a plurality of suture guides 48A, 48B, 50B, 52A, 52B. spaced about the frame 42. While the suture guides 48A-52B may each be used with individual sutures, it is also very useful for the sutures guides 48A, 48B; 50A, 50B; and 52A, 52B to comprise pairs of suture guides 48, 50, and 52, respectively. As will be discussed later in this specification, each of the pairs of suture guides 48, 50, 52 can be used with the ends of a single suture.

In the embodiment shown in FIGS. 1 and 2, the frame 42 also comprises a plurality of tabs 54A, 54B, 54C, 54D which protrude from the frame 42. In this embodiment, at least some of the suture guides 48B, 50A, 50B, 52B are located in respective tabs 54A, 54B, 54C, 54D. Depending on your perspective, the ends 56A, 56B of the frame 42 could also be considered tabs in which respective suture guides 48A, 52A have been formed.

Generally, the interior of the frame 42 will be the area of surgical focus when the device 40 for cardiac surgery is used. In this embodiment, the tabs 54A-54D protrude from the frame 42 towards an inner side of the frame.

Figure 3:
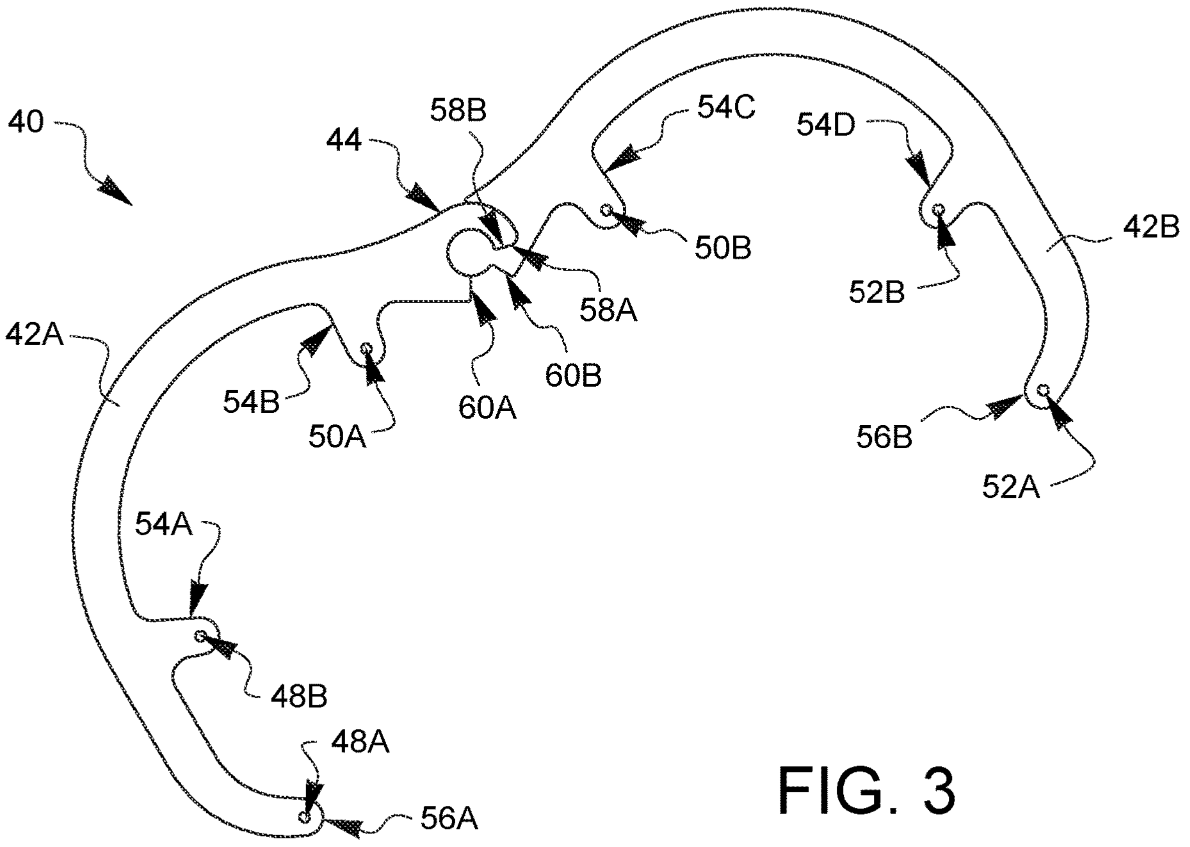
FIGS. 3 and 4 are top views of the device for cardiac surgery from FIG. 1, the views illustrating the device in an opened and a closed position, respectively.
Figure 4:
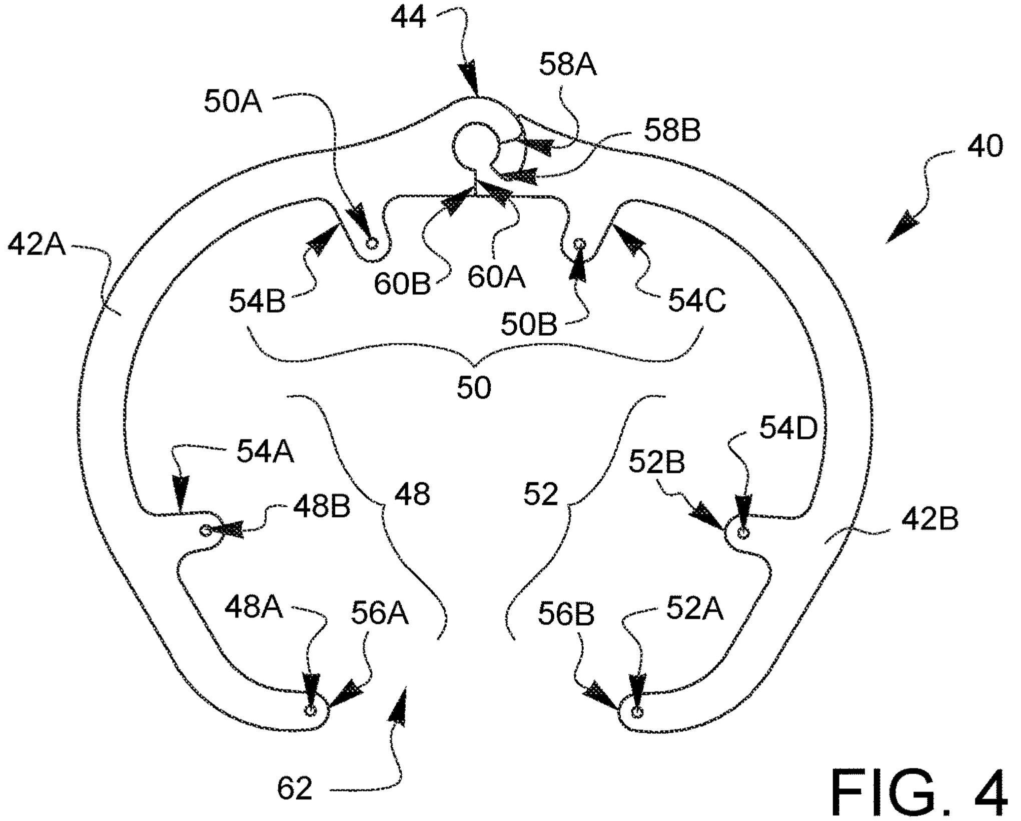

FIGS. 3 and 4 are top views of the device 40 for cardiac surgery from FIG. 1, the views illustrating the device 40 in an opened and a closed position, respectively. In the open position of FIG. 3, the first and second frame parts 42A, 42B have pivoted relative to each other about the hinge 44 until a first open stop 58A and a second open stop 58B contact each other. The first open stop 58A is defined by the first frame part 42A, while the second open stop 58B is defined by the second frame part 42B. In this open position (or any of the intervening positions leading up to the fully open position of FIG. 3), the device 40 may more easily be passed from outside the patient, through a minimally invasive opening, and into an interior cavity of the patient, such as the pericardial cavity. In this embodiment, the hinge 44 enables the two parts of the frame 42A, 42B to open like a jaw.

In the closed position of FIG. 4, the first and second frame parts 42A, 42B have pivoted relative to each other about the hinge 44 until a first closed stop 60A and a second closed stop 60B contact each other. The first closed stop 60A is defined by the first frame part 42A, while the second closed stop 60B is defined by the second frame part 42B. In this closed position, the device 40 is oriented for use in a cardiac operation, an example of which will be described below. As can be seen in FIG. 4, in this embodiment, the frame forms a substantially continuous periphery with one open side 62. The frame in this embodiment also has a substantially rounded shape. In this embodiment, the plurality of suture guides 48A, 48B, 50A, 52A, 52B are also aligned to fall substantially on a same circle. Looked at as pairs of suture guides 48, 50, 52, in this embodiment, the pairs of suture guides are spaced substantially evenly around a centerpoint of such circle.

Figure 5A:
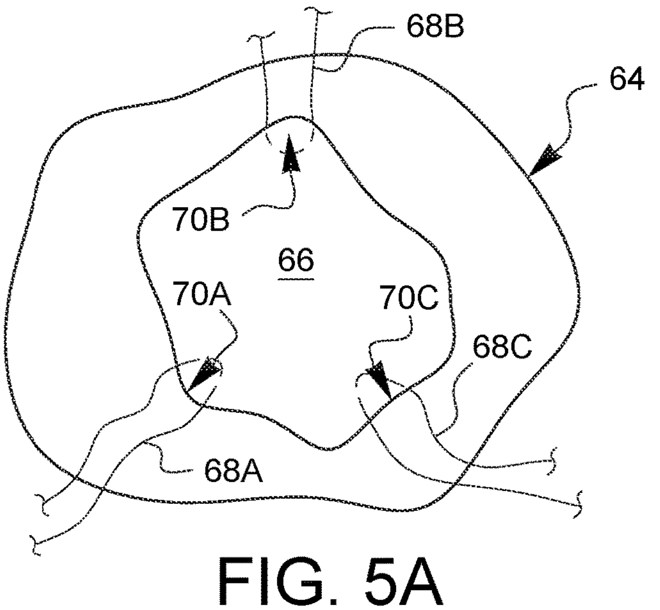
FIGS. 5A-5D illustrate one embodiment of a surgical setting and a surgical method where the device for cardiac surgery from FIG. 1 finds utility.

FIGS. 5A-5D illustrate one embodiment of a surgical setting and a surgical method where the device for cardiac surgery from FIG. 1 finds utility. FIG. 5A schematically illustrates a surgical situation. Minimally invasive surgical access has been gained on a patient, for example, through a right atrial mini-thoracotomy (access between two of the patient's ribs). An incision has been made in the aorta 64, creating an opening through which the aortic valve and the left ventricle 66 may be accessed. The aortic valve is not visible in FIG. 5A because the valve leaflets were diseased and have been removed. First, second, and third stay sutures 68A, 68B, 68C have been placed by the surgeon at the locations of the valve commissures 70A, 70B, respectively. The commissures 70A, 70B, 70C are the location on the aortic root where the bases of different valve leaflets (now removed) used to come together.

Figure 5B:
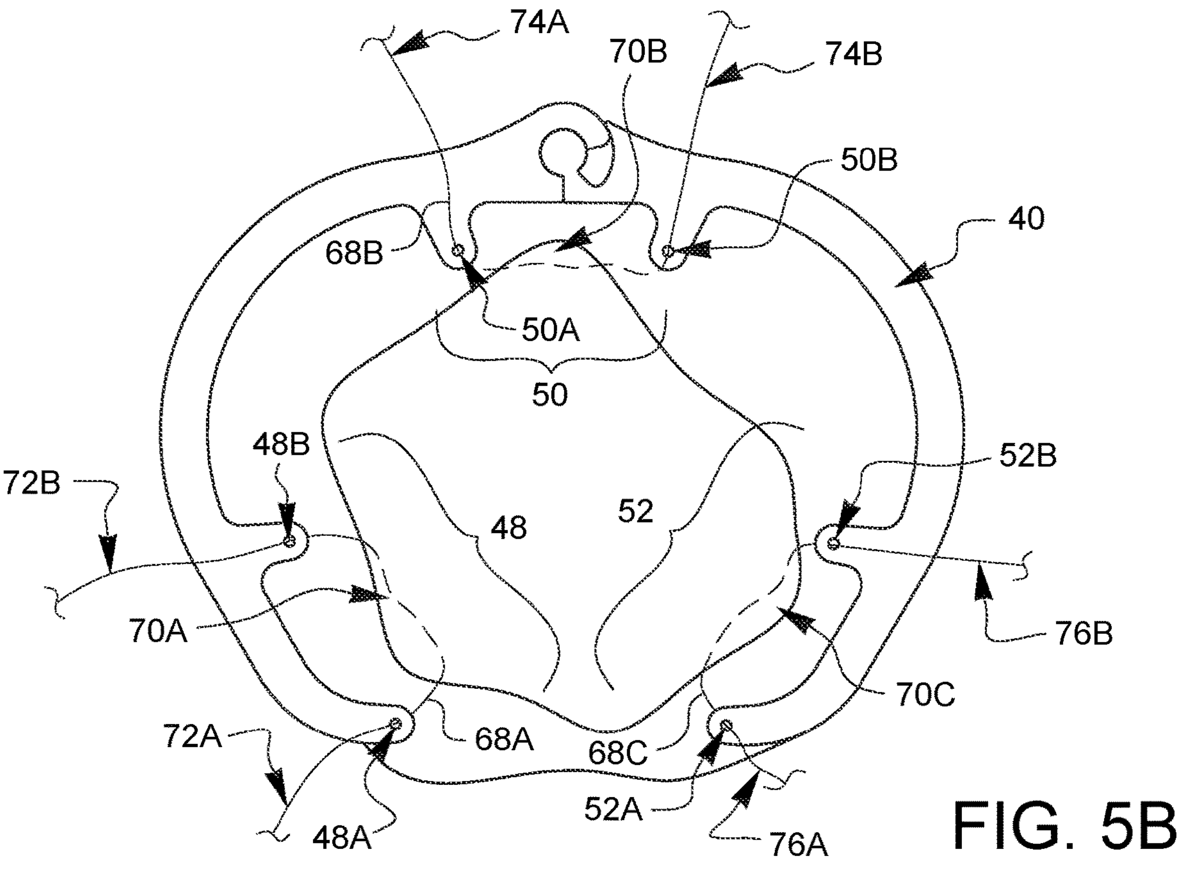

In FIG. 5B, the device 40 for cardiac surgery has been positioned against the heart in a closed position, around the surgical opening in the aorta such that the pairs of suture guides 48, 50, 52 are generally aligned with the stitches in the commissures 70A, 70B, 70C. The first and second ends 72A, 72B of the first stay suture 68A are passed through respective first and second suture guides 48A, 48B in the first pair of suture guides 48. Similarly, the first and second ends 74A, 74B of the second stay suture 68B are passed through respective first and second suture guides 50A, 50B in the second pair of suture guides 50. Similarly, the first and second ends 76A, 76B of the third stay suture 68C are passed through respective first and second suture guides 52A, 52B in the third pair of suture guides 52. The suture ends may be passed through their respective guides using a needle (not shown) or by using a snare (also not shown).

Figure 5C:
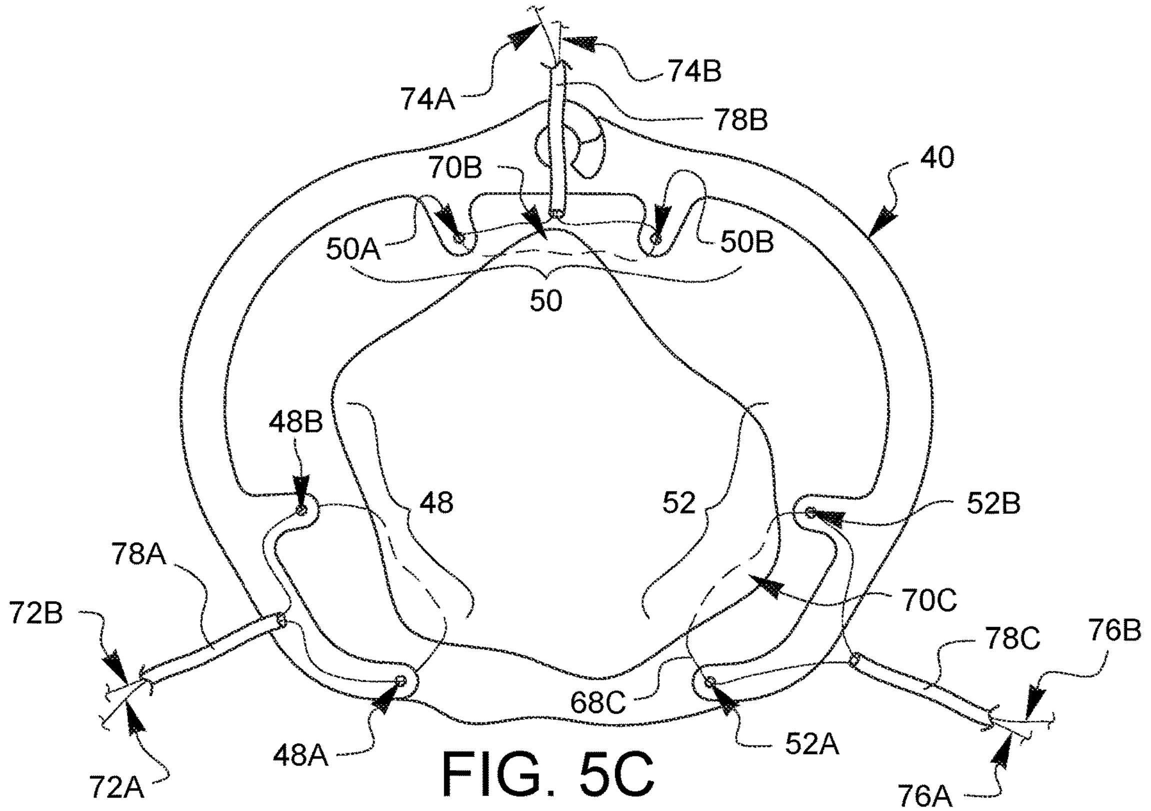
Figure 5D:
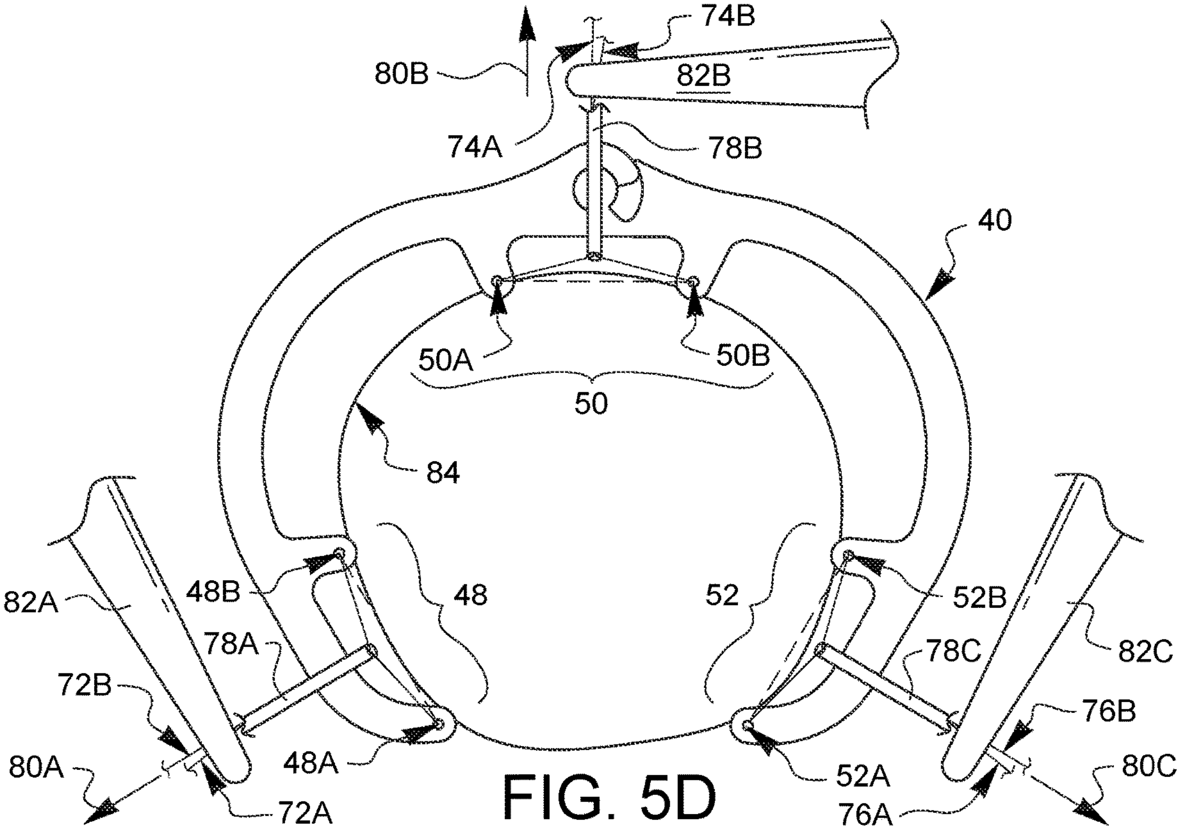

In FIG. 5C, the first and second suture ends 72A, 72B of the first stay suture 68A have further been passed through a first suture tube 78A. Similarly, the first and second suture ends 74A, 74B of the second stay suture 68B have further been passed through a second suture tube 78B. Similarly, the first and second suture ends 76A, 76B of the third stay suture 68C have further been passed through a third suture tube 78C. The suture ends may be passed through their respective suture tubes using a snare (not shown). Suitable tubes include flexible or rigid tubes which may be used in the fashion of a Rumel tourniquet as known to those skilled in the art. FIG. 5D illustrates one example of such tourniquet usage. The first suture ends 72A, 72B of the first stay suture 68A may be tensioned 80A while the first suture tube 78A is held. A first clamp 82A is placed on the suture ends 72A, 72B at the end of the suture tube 78A to maintain the tension in the first stay suture 68A. Similarly, The suture ends 74A, 74B of the second stay suture 68B may be tensioned 80B while the second suture tube 78B is held. A second clamp 82B is placed on the suture ends 74A, 74B at the end of the suture tube 78B to maintain the tension in the second stay suture 68B. Similarly, the suture ends 76A, 76B of the third stay suture 68C may be tensioned 80C while the third suture tube 78C is held. A third clamp 82C is placed on the suture ends 76A, 76B at the end of the suture tube 78C to maintain the tension in the third stay suture 68C. The tension on the sutures can be adjusted as desired to draw out the aortic root 84. Further suture stitches will need to be placed around the circumference of the aortic root 84 in order to attach a replacement aortic valve. The device 40 for cardiac surgery helps to draw this target tissue out and improve visualization of both the aortic root and the area of interest for the aortic valve replacement. The suture tubes 78A-78C may also be used as manipulators to help position the underlying tissue by moving the device 40 to which the tissue is attached.

Figure 6:
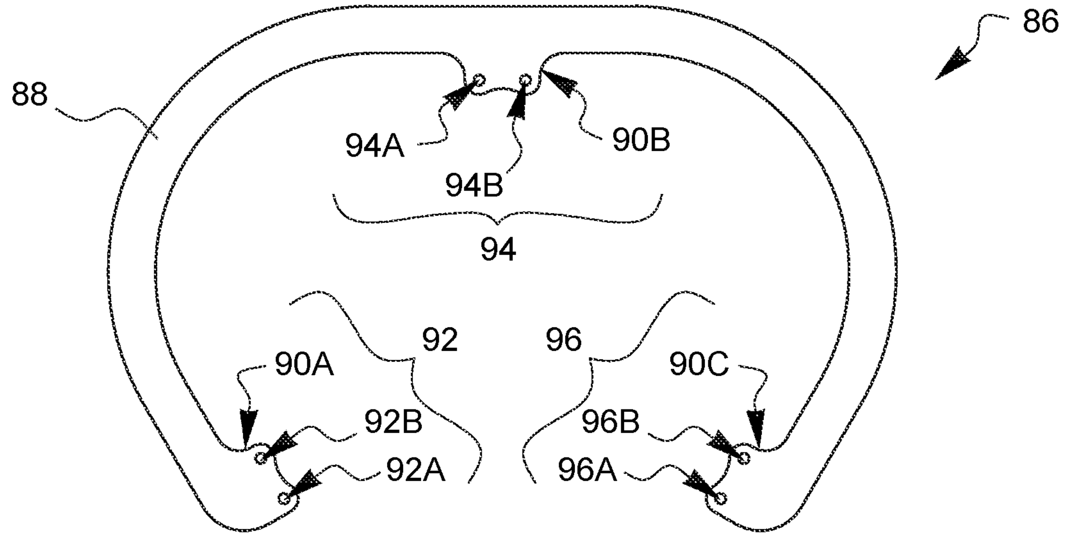
FIG. 6 is a top view of another embodiment of a device for cardiac surgery, this embodiment being one fixed piece and having the suture guides in each pair of suture guides spaced more closely together than the embodiment of FIG. 1.

FIG. 6 is a top view of another embodiment of a device 86 for cardiac surgery. The device 86 has a frame 88 that is a single piece. In this embodiment, the frame has first, second, and third tabs 90A, 90B, 90C which protrude inward. Suture guides 92A, 92B make up a first pair of suture guides 92. Suture guides 94A, 94B make up a second pair of suture guides 94. Suture guides 96A, 96B make up a third pair of suture guides 96. Each of the first, second, and third pairs of suture guides 92, 94, 96 are located on a respective first, second, and third tab 90A, 90B, 90C of the frame 88. As compared to the earlier embodiment, in this embodiment, the suture guides in a given pair of suture guides are also closer together. In this embodiment, however, the pairs of suture guides 92, 94, 96 are still spaced substantially equally around an imaginary circle through which all of the suture guides pass.

Figure 7:
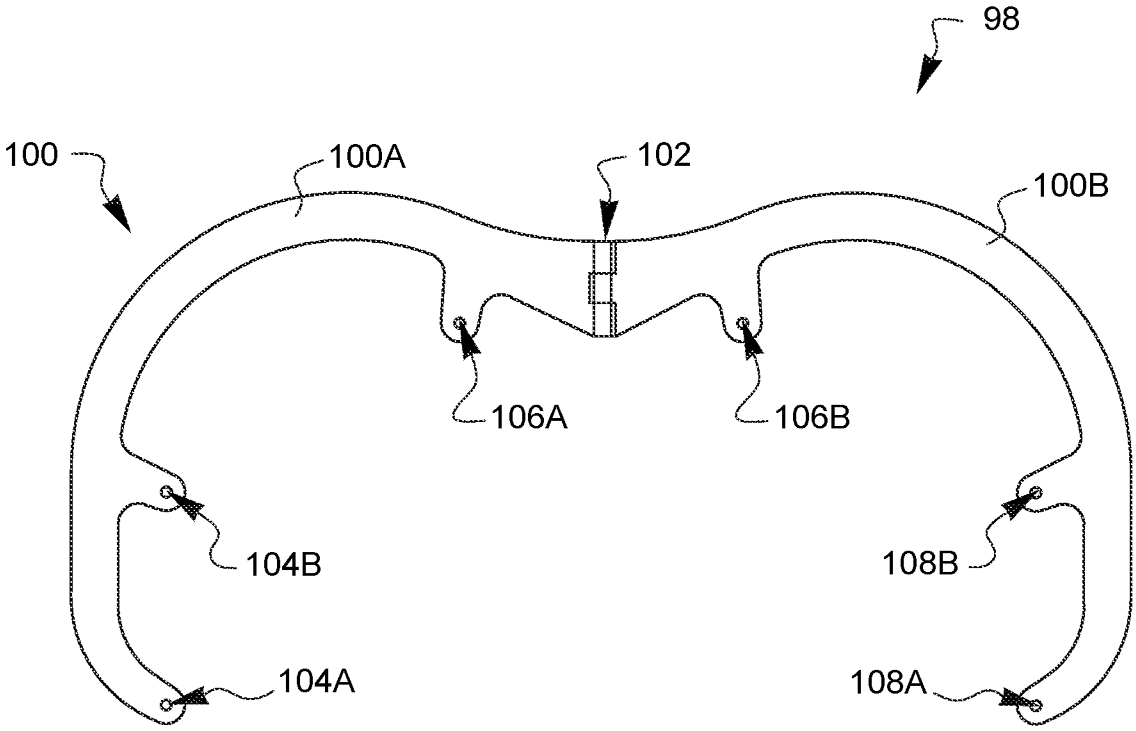
FIG. 7 is a top view of a further embodiment of a device for cardiac surgery, this embodiment being hinged in a different manner as compared to the embodiment of FIG. 1.

FIG. 7 is a top view of a further embodiment of a device 98 for cardiac surgery. The device 98 has a frame 100 which comprises first and second frame parts 100A, 100B. The first and second frame parts 100A, 100B are pivotably coupled together by a hinge 102 that enables the two parts of the frame 100A, 100B to fold on themselves like a book. FIG. 7 shows the frame 100 in an opened position, but in a folded position, the frame can take up less space and be easier to pass through a minimally invasive surgical opening. Like previous embodiments, the device 98 of FIG. 7 has a plurality of suture guides 104A, 104B, 106A, 106B, and 108A, 108B distributed around the frame 100.

Figure 8:
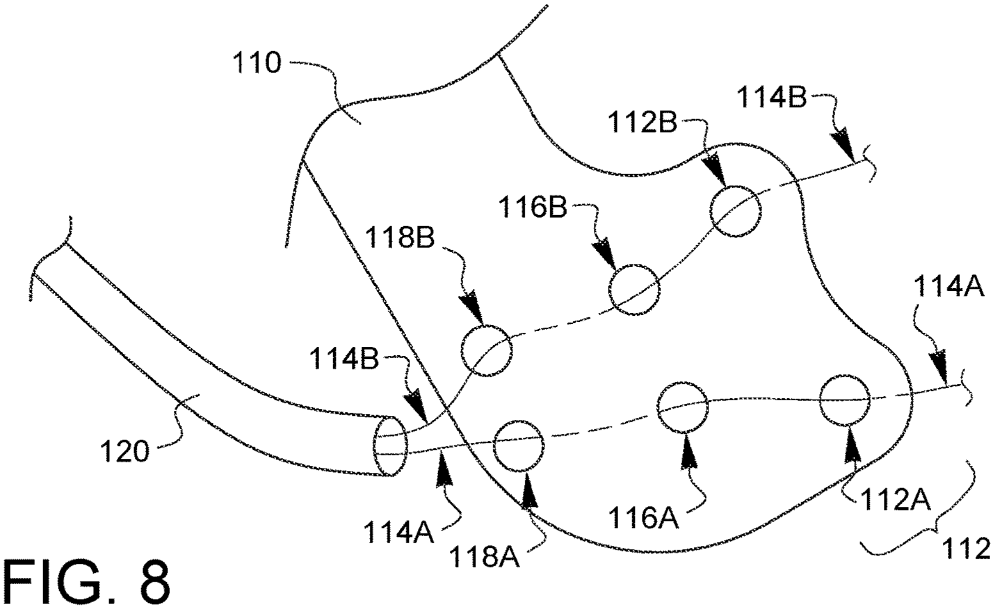
FIG. 8 is a top view of a portion of a frame on another embodiment of a device for cardiac surgery, this embodiment having a different arrangement of suture guides as compared to previous embodiments.

FIG. 8 is a top view of a portion of a frame 110 on another embodiment of a device for cardiac surgery. In the position of the frame 110 shown in FIG. 8, there are first and second initial suture guides 112A, 112B which make up a pair of initial suture guides 112. Each of the initial suture guides 112A, 112B is configured to accept suture that has been placed in a tissue. For example, as shown in FIG. 8, first and second suture ends 114A, 114B, which come from the same suture that has been stitched into a portion of tissue (not shown), have been passed up through the respective initial suture guides 112A, 112B. The frame 110 also has a plurality of secondary suture guides, each configured to accept suture from at least one of the initial suture guides 112A, 112B or from at least another of the secondary suture guides. In this embodiment, the first suture end 114A, after having been passed up through the initial suture guide 112A as described, is then passed down through the secondary suture guide 116A and back up through the secondary suture guide 118A. Similarly, the second suture end 114B, after having been passed up through the initial suture guide 112B as described, is then passed down through the secondary suture guide 116B and back up through the secondary suture guide 118B. The suture ends 114A, 114B can then be passed through a suture tube 120 as described with previous embodiments. One possible advantage of the initial and secondary suture guide system of the embodiment in FIG. 7 is that it allows for a different spacing between the pair of initial suture guides 112A, 112B which interface more directly with the tissue as compared to the spacing between the pair of secondary suture guides 118A, 118B which interface more directly with the suture tube 120. In this embodiment, the pair of secondary suture guides 118A, 118B are spaced more closely together than the pair of initial suture guides 112A, 112B. In some embodiments, such as this one, a wider spacing of the initial suture guides 112A, 112B may be more desirable to spread out the stay suture pulling lines for shaping/positioning the aortic root. In some embodiments, such as this one, a more narrow spacing of the secondary suture guides 118A, 118B which interface with the suture tube 120 may be more desirable because it more closely couples the suture tube 120 to the frame 110 when the suture ends 114A, 114B are under tension. The secondary suture guides also enable the suture tube 120 to be located farther away from the inner side of the frame 110, which may afford more space for a fragile replacement heart valve to be worked into place without worry of contacting the suture tubes. In still other embodiments, the one or more secondary suture guides can act as alternate primary suture guides, providing a surgeon choices for positioning of the suture when threading it through the primary suture guide of choice.

Figure 9:
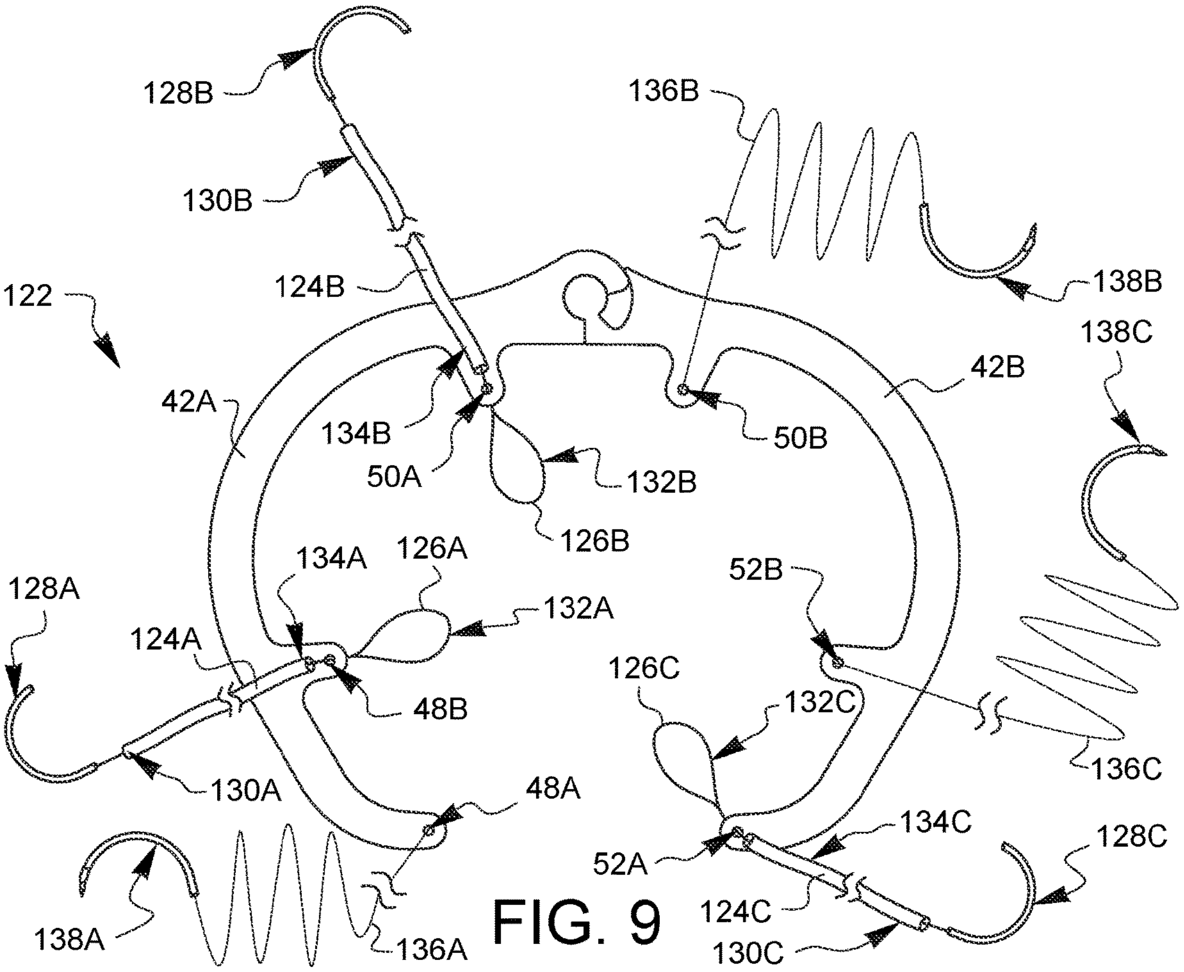
FIG. 9 is a schematic view of a further embodiment of a device for cardiac surgery.

FIG. 9 is a schematic view of a further embodiment of a device 122 for cardiac surgery. The embodiment of FIG. 9 has many elements in common with the embodiment of FIG. 1. For efficiency, the similar elements in the embodiment of FIG. 9 will include similar identifying numbers and their description will not be repeated. The device 122 has a plurality of suture tubes 124A, 124B, 124C which correspond, respectively, to one of the pairs of suture guides 48, 50, 52. The device 122 also has a plurality of snares 126A, 126B, 126C, each corresponding to and passed through a respective suture tube 124A, 124B, 124C. Each of the snares 126A, 126B, 126C has a respective handle 128A, 128B, 128C protruding through a respective proximal end 130A, 130B, 130C of the corresponding respective suture tube 124A, 124B, 124C. Although the snare handles 128A, 128B, 128C are illustrated as something separate from the snare wires in this embodiment, the handles could simply be the ends of the snare or formed from the ends of the snare in other embodiments. Each of the snares 126A, 126B, 126C also has a respective snare loop 132A, 132B, 132C at the other end of the respective snare 126A, 126B, 126C and protruding through a respective distal end 134A, 134B, 134C of the respective corresponding suture tube 124A, 124B, 124C, and wherein each of the snare loops 132A, 132B, 132C further protrudes through a respective one of the suture guides 48B, 50A, 52A in a corresponding, respective pair of suture guides 48, 50, 52.

The device 122 also has a plurality of sutures 136A, 136B, 136C, each corresponding to one of the respective pairs of suture guides 48, 50, 52 and coupled to the respective suture guide 48A, 50B, 52B which does not have a snare loop 132A, 132B, 132C passing through it. Each of the sutures 136A, 136B, 136C has a respective needle 138A, 138B, 138C coupled to an end of the suture opposite the other end of the suture which is coupled to the corresponding suture guide. Each of the suture guides 48A, 50B, 52B to which the suture is coupled may be referred to as a suture anchor point. Sutures may be coupled to the suture anchor point (a suture guide) by a tied knot or a mechanical knot. One suitable example of a mechanical knot is the Ti-KNOT® device or the COR-KNOT® device which is manufactured and sold by LSI Solutions, Inc. of Victor, NY (see www.lsisolutions.com). In some embodiments, if a mechanical knot is used, the mechanical knot may be coupled to the frame.

One advantage of the device 122 is that it has many of the necessary elements already combined into one assembly. Once the device frame 42 is situated adjacent to the tissue to be worked on, each of the sutures 136A, 136B, 136C may be stitched through a respective commis sure of the aortic root, the needles may then be removed from the suture, and then the suture ends where the needles used to be attached may be threaded through a respective snare loop 132A, 132B, 132C in order to draw each of the single suture ends out through a respective suture tube 124A, 124B, 124C. The single suture ends can then be clamped at each respective proximal end 130A, 130B, 130C of the suture tubes 124A, 124B, 124C after the desired suture tension is achieved.

Figure 10:
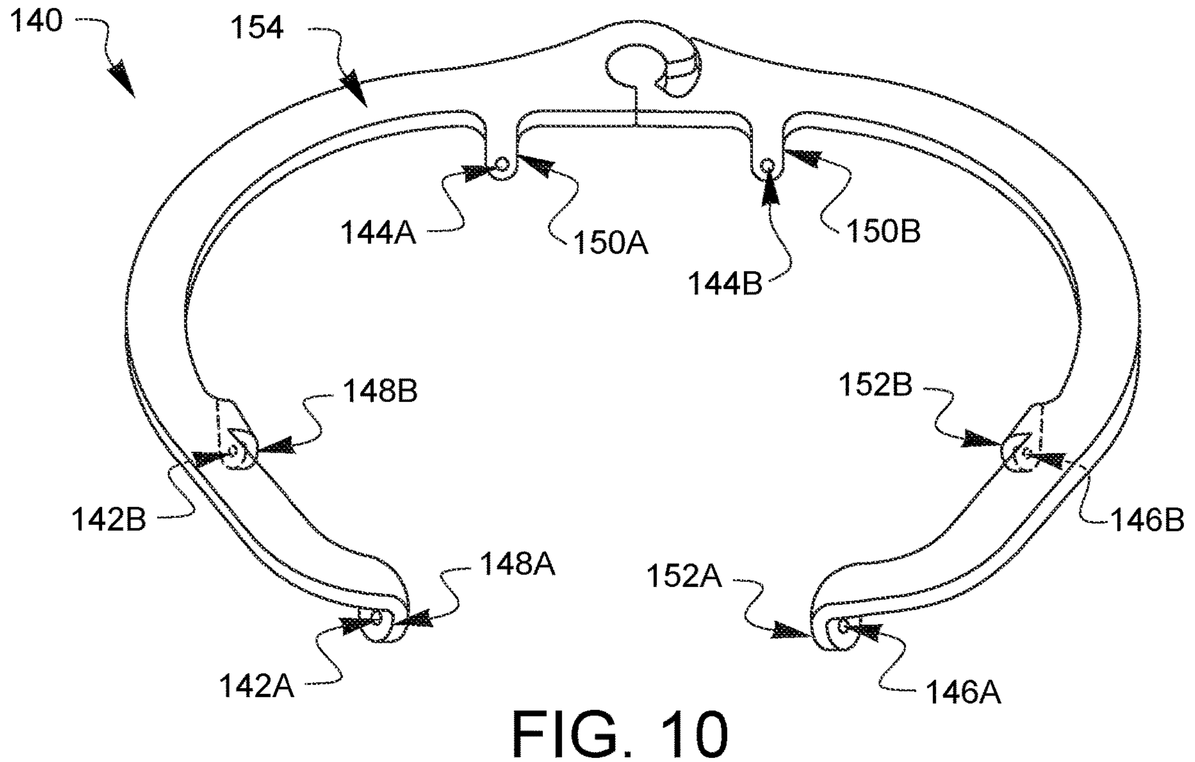
FIG. 10 is a perspective view of another embodiment of a device for cardiac surgery, this embodiment having suture guides located on frame tabs which are bent out of a plane which the remainder of the frame occupies.

FIG. 10 is a perspective view of another embodiment of a device 140 for cardiac surgery. This embodiment is similar to the embodiment of FIG. 1, with the exception that the suture guides 142A, 142B, 144A, 144B, 146A, 146B are located on respective frame tabs 148A, 148B, 150A, 150B, 152A, 152B which are bent out of a plane which the remainder of the frame 154 occupies. These bent tabs 148A, 148B, 150A, 150B, 152A, 152B can allow the frame to sit on one part of the heart and/or other adjacent tissue while the tabs 148A, 148B, 150A, 150B, 152A, 152B move the suture guides 142A, 142B, 144A, 144B, 146A, 146B closer to the aortic root. In other embodiments, the tabs could be bent upwards.

Figure 11:
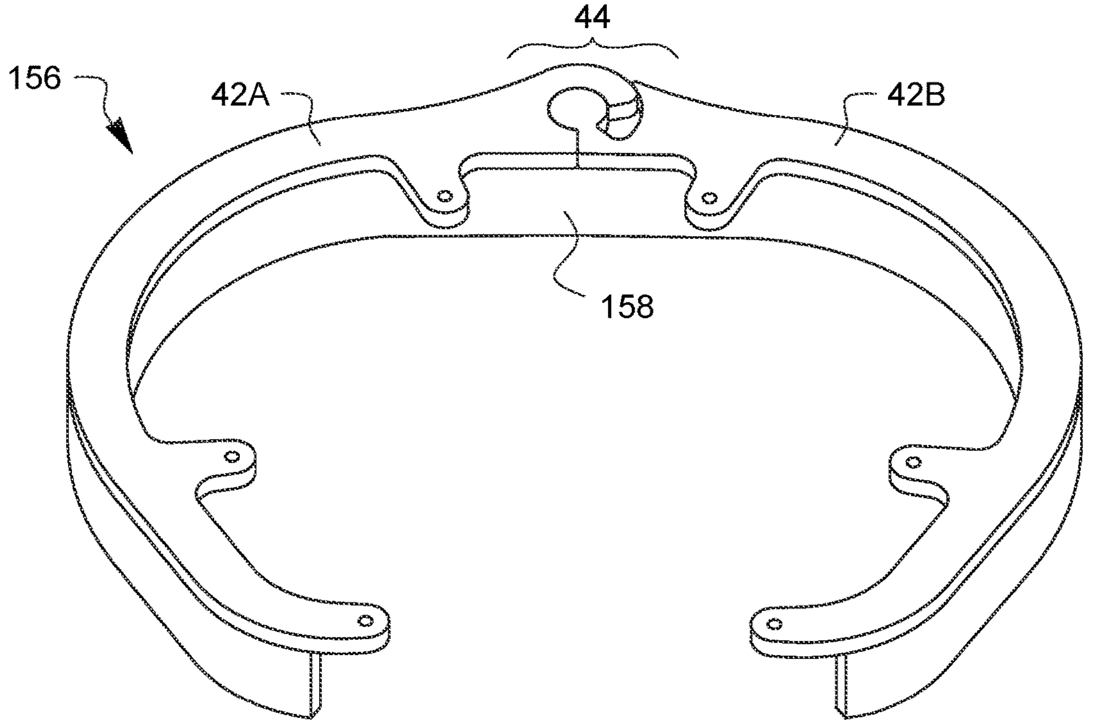
FIG. 11 is a perspective view of a further embodiment of a device for cardiac surgery, this embodiment having a skirt coupled to the frame.

FIG. 11 is a perspective view of a further embodiment of a device 156 for cardiac surgery. This embodiment is similar to the embodiment of FIG. 1, with the addition of a skirt 158 coupled to both parts of the frame 42A, 42B. The skirt 158 can have a variety of dimensions and cross-sectional shapes. The skirt 158 can act as a softer tissue interface and may even be absorbent in some embodiments to help keep a surgical field clear. The skirt 158 may also have a resilient shape (elasticity) so that it can also act as a spring member to help return or bias the frame parts 42A, 42B to a closed (operating) position in the absence of some greater opening force being applied about the hinge 44.

Figure 12:
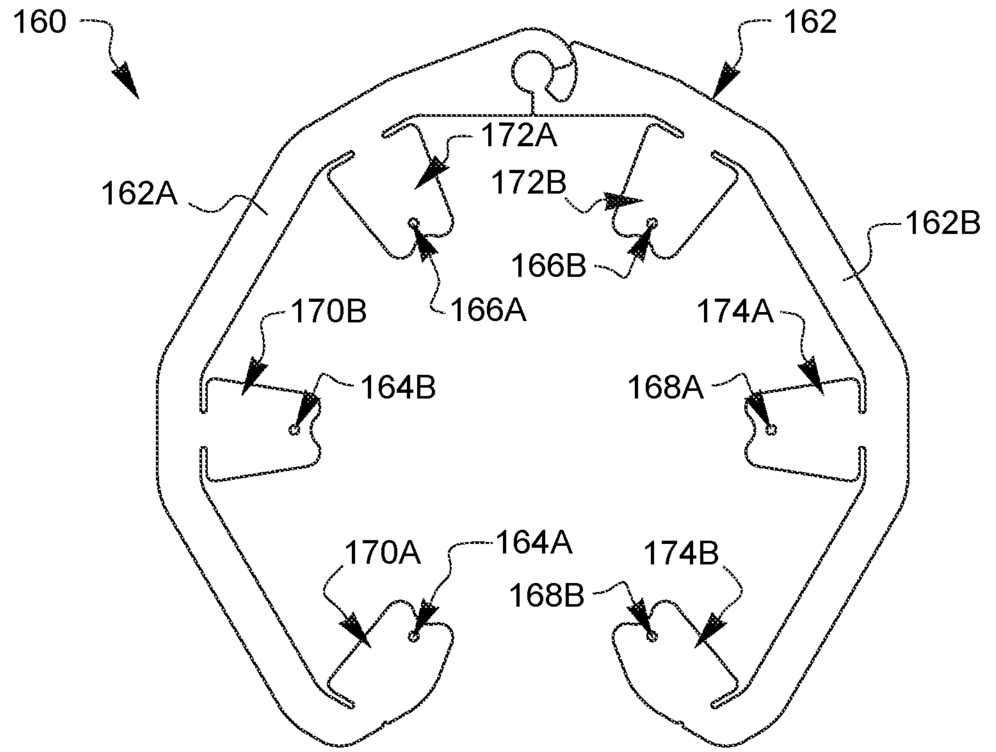
FIGS. 12 and 13 are top views of another embodiment of a device for cardiac surgery, shown in closed and open positions, respectively, and having substantially equal suture guide spacing in the closed position.
Figure 13:
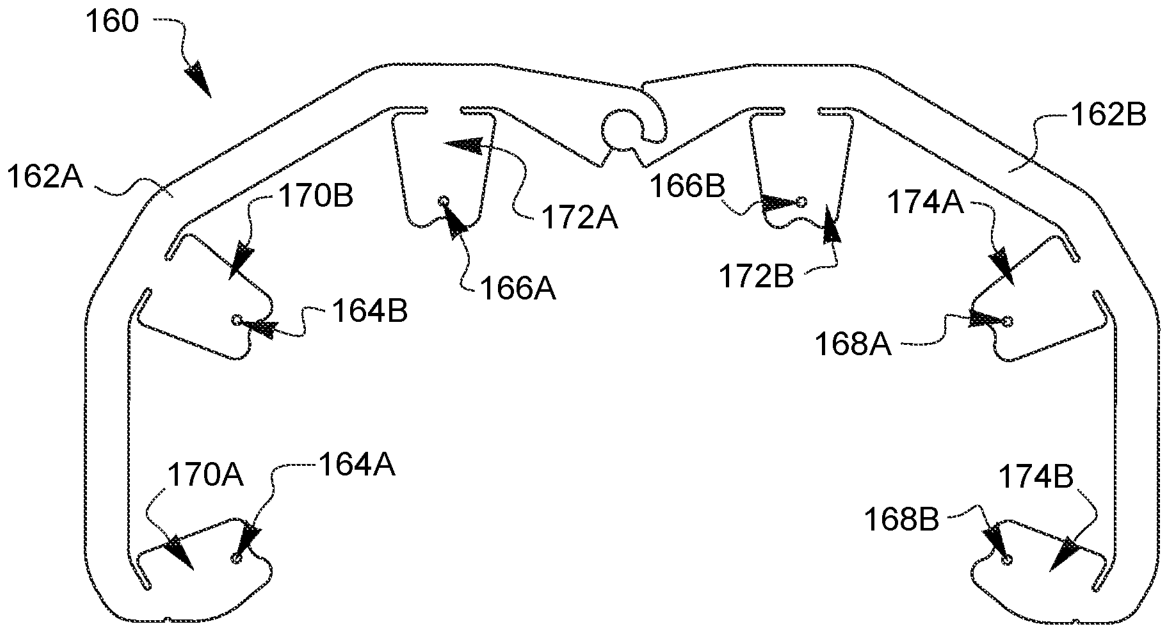

FIGS. 12 and 13 are top views of another embodiment of a device 160 for cardiac surgery, shown in closed and open positions, respectively. The embodiment of FIGS. 12 and 13 is similar to the embodiment of FIG. 1, but the frame 162 (comprising first and second frame parts 162A, 162B) has a substantially polygonal shape when in the closed (operating) position of FIG. 12. Similar to the embodiment of FIG. 1, the device 160 of FIGS. 12 and 13 has a plurality of suture guides 164A, 164B, 166A, 166B, 168A, 168B, each of which is located on a respective tab 170A, 170B, 172A, 172B, 174A, 174B. In this embodiment, however, the suture guides 164A, 164B, 166A, 166B, 168A, 168B are distributed substantially equally around a circle through which they all pass (approximately every 60 degrees).

While the tabs 170A, 170B, 172A, 172B, 174A, 174B of the device 160 lie substantially in the same plane as the frame 162, the tabs 170A, 170B, 172A, 172B, 174A, 174B may be configured to be bent, thereby enabling a surgeon to customize the position of the suture guides 164A, 164B, 166A, 166B, 168A, 168B relative to the frame in order to accommodate differing patient anatomies. In some embodiments, the tabs may be pre-bent in a recommended or starting configuration. In some embodiments, one or more of the tabs may be configured to be bent in more than one location.

Figure 14A:
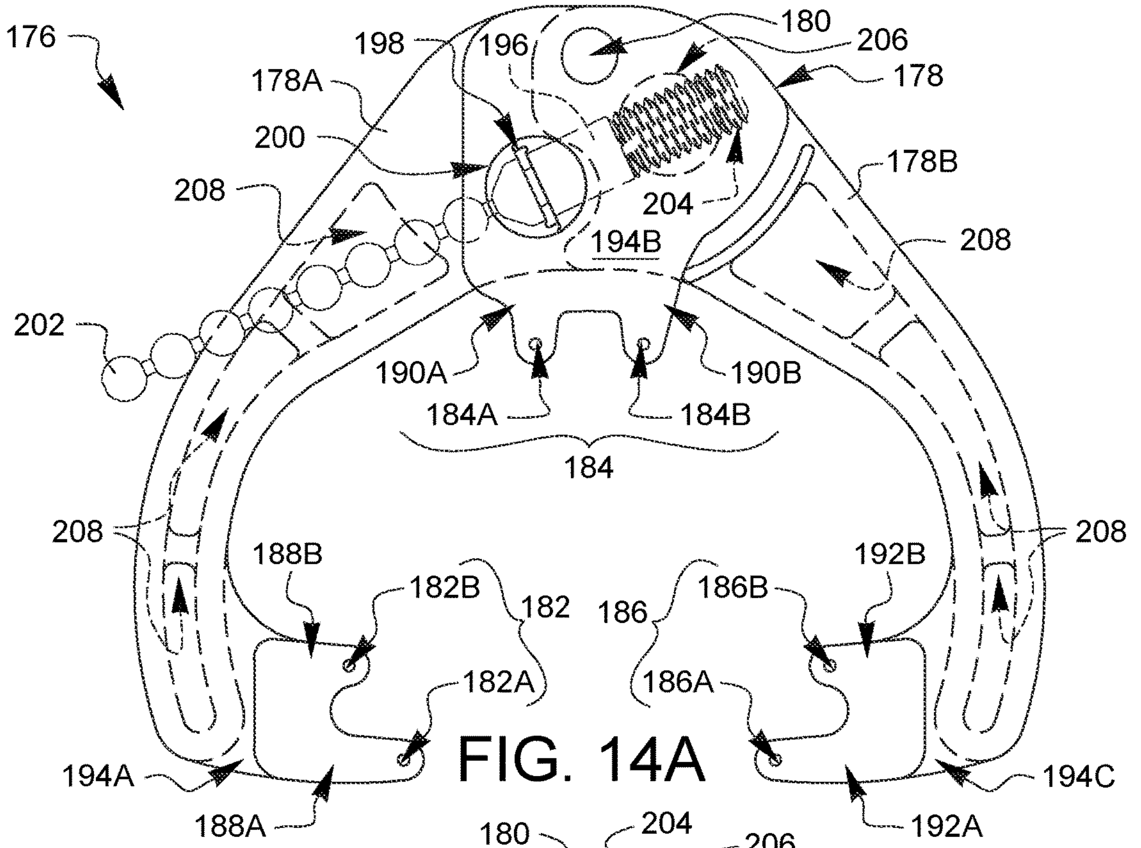
FIGS. 14A and 14B are top views of a further embodiment of a device for cardiac surgery, the views illustrating the device in a closed and an opened position, respectively.
Figure 14B:
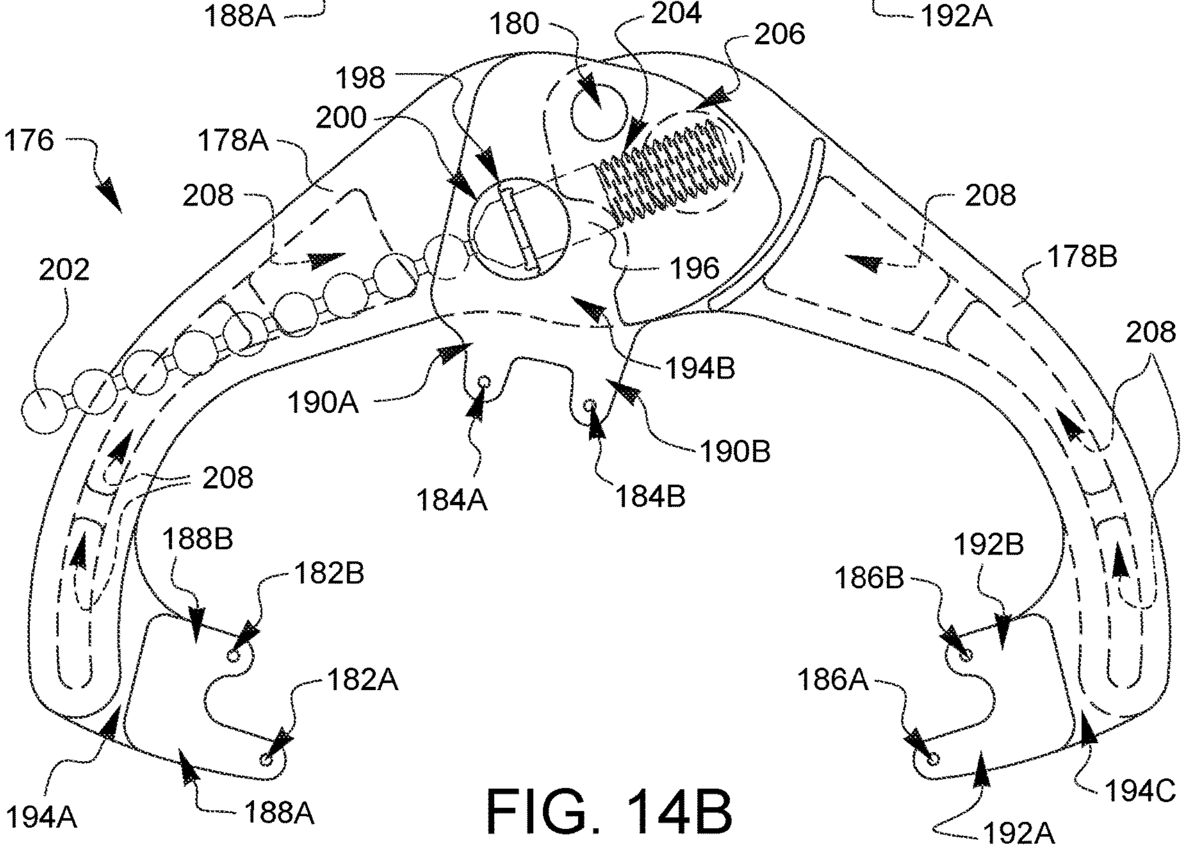

FIGS. 14A and 14B are top views of a further embodiment of a device 176 for cardiac surgery, the views illustrating the device in a closed and an opened position, respectively. The device 176 has a frame 178 which comprises first and second frame parts 178A, 178B. The first and second frame parts 178A, 178B are pivotably coupled together by a hinge point 180.

The device 176 for cardiac surgery also has a plurality of suture guides 182A, 182B, 184A, 184B, 186A, 186B spaced about the frame 178. While the suture guides 182A-186B may each be used with individual sutures, it is also very useful for the sutures guides 182A, 182B; 184A, 184B; and 186A, 186B to comprise pairs of suture guides 182, 184, and 186, respectively. As with previous embodiments in this specification, each of the pairs of suture guides 182, 184, 186 can be used with the ends of a single suture.

In the embodiment shown in FIGS. 14A and 14B, the frame 178 also comprises a plurality of tabs 188A, 188B, 190A, 190B, 192A, 192B which protrude from the frame 178. In this embodiment, the tabs 188A-192B are raised up to a different plane than the first and second frame parts 178A, 178B by extensions 194A, 194B, 194C. Other embodiments might not have extensions and the tabs could lie in substantially the same plane. In still other embodiments, the tabs could be bendable or bent in such a way as to allow at least some of the suture guides to be in a substantially different plane from the first and second frame parts 178A, 178B. In this embodiment, the suture guides 182A, 182B, 184A, 184B, 186A, 186B are located in respective tabs 188A, 188B, 190A, 190B, 192A, 192B.

In this embodiment, the device 176 also has a drive screw 196 which has a groove (not visible in these views) which is held by a clip 198 within a cylindrical plug 200 pivotably coupled within the first frame part 178A. The drive screw 196 can be rotated within the cylindrical plug 200, but cannot translate due to the clip 198. A flexible drive extension 202 may be coupled to the drive screw 196 for remotely turning the drive screw 196. The drive screw 196 has threads 204 which engage a threaded cylindrical plug 206 that is pivotably coupled to the second frame part 178B. Therefore, when the drive screw 196 is turned in a first direction, the first and second frame parts 178A, 178B will tend to close towards a closed position such as illustrated in FIG. 14A. Similarly, when the drive screw 196 is turned in a second direction, the first and second frame parts 178A, 178B will tend to open towards an opened position such as illustrated in FIG. 14B.

In the embodiment of FIGS. 14A, 14B, the first and second frame parts 178A, 178B have one or more voids 208 which open to the underside of the frame parts 178A, 178B. Corresponding skirt material may be inserted into the one or more voids 208 in order to provide a more compliant tissue interface for the device 176.

Figure 15:
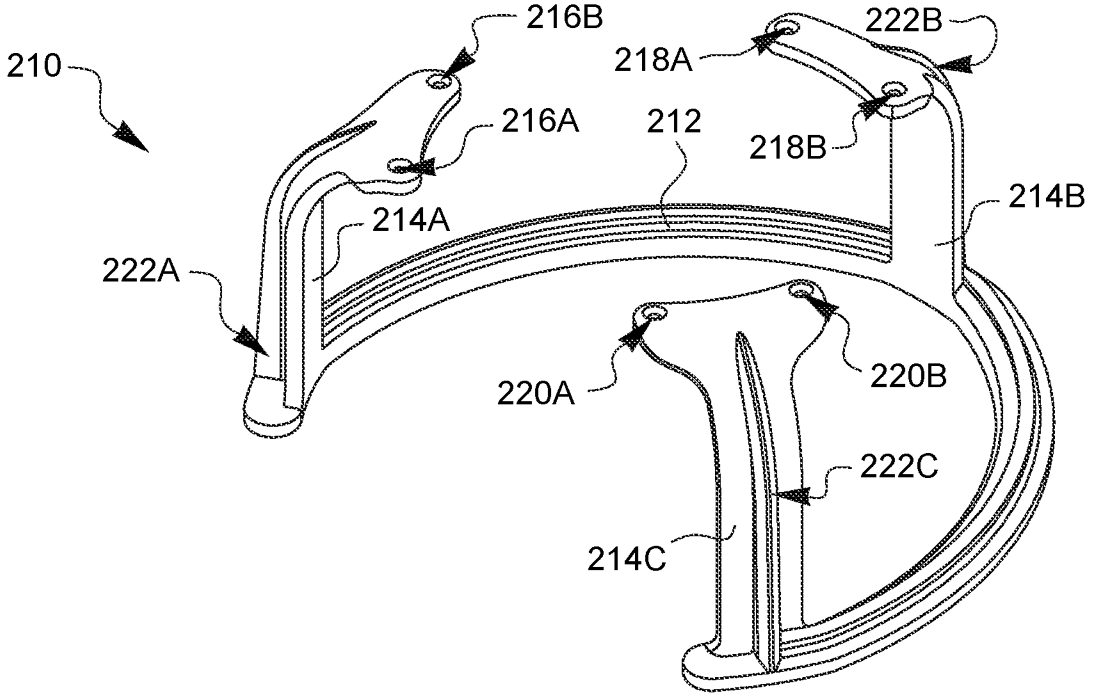
FIGS. 15 and 16 are perspective and top views, respectively, of another embodiment of a device for cardiac surgery.
Figure 16:
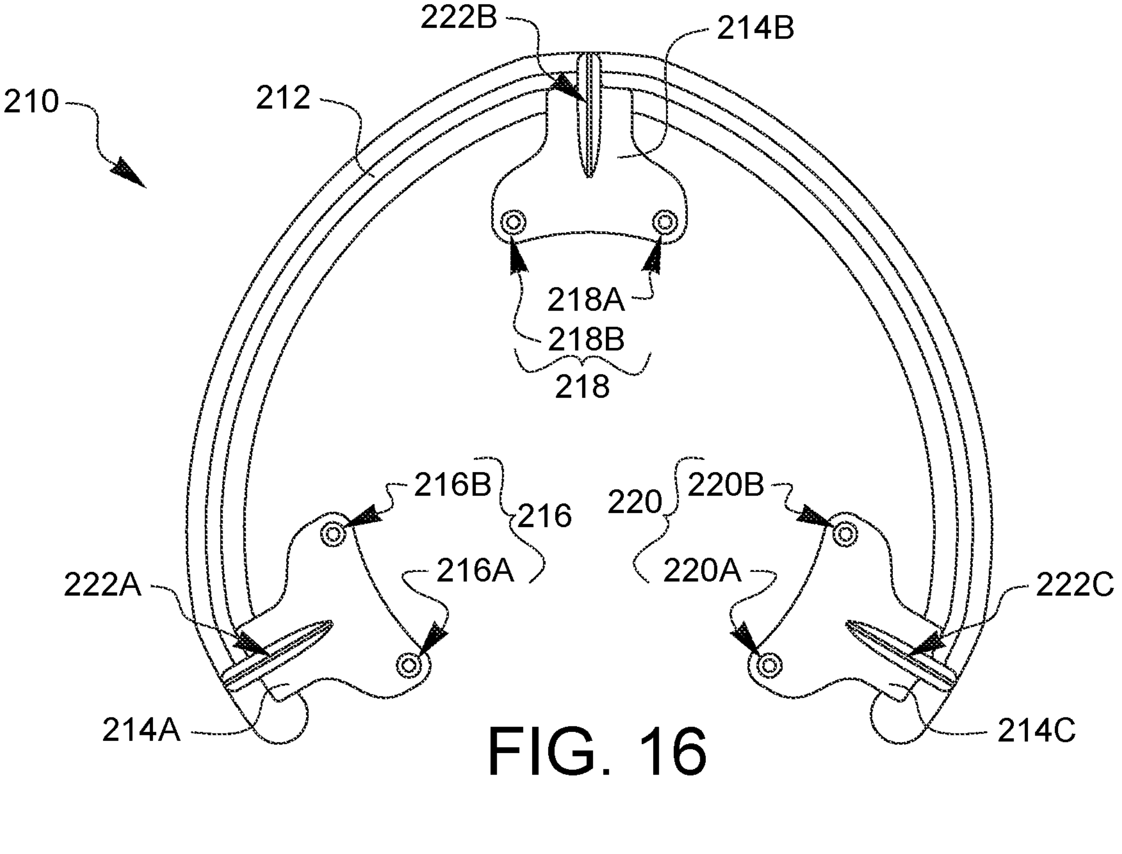
Figures 17A, 17B, 17C, 17D, 17E, 17F:
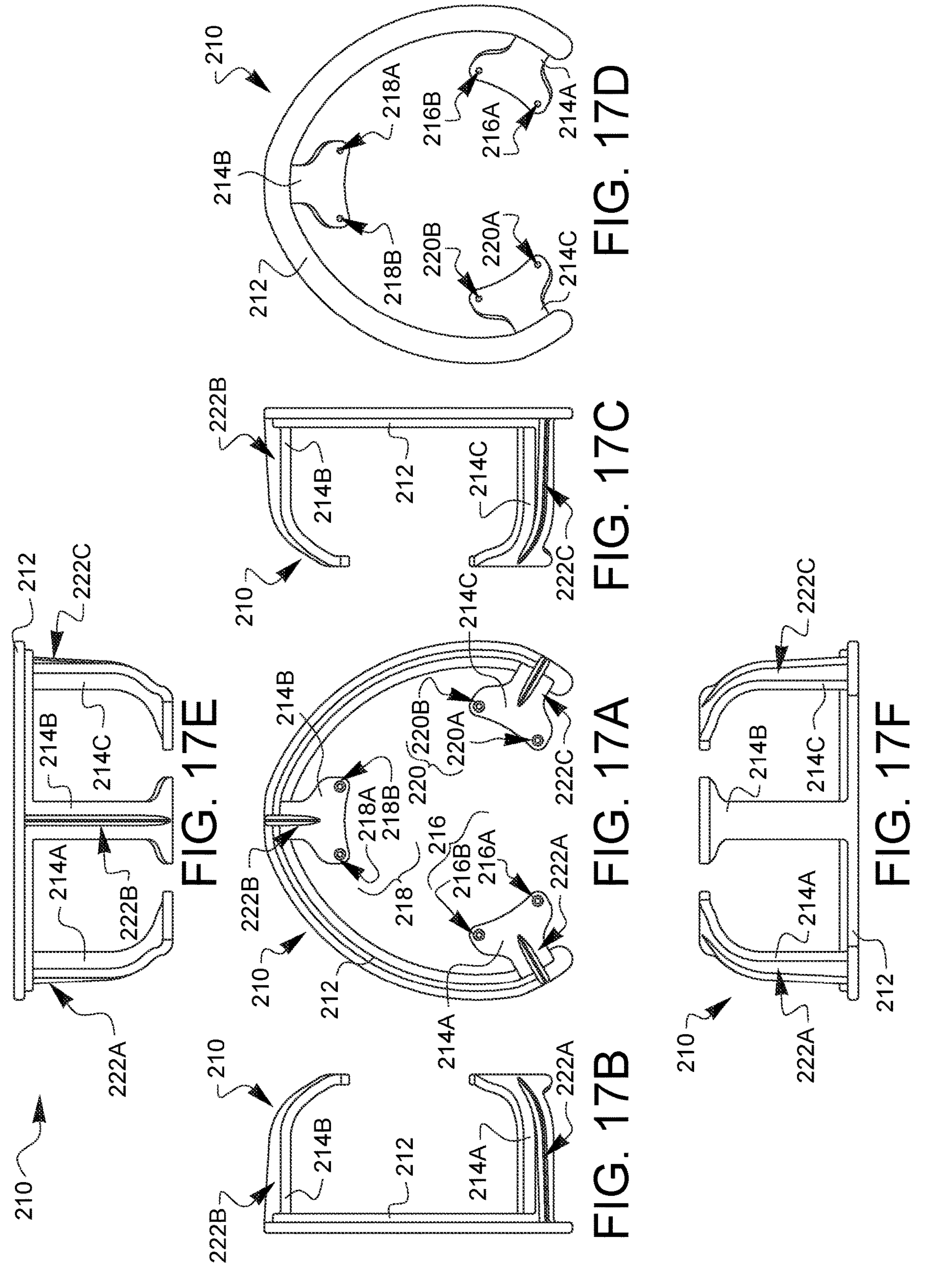
FIGS. 17A, 17B, 17C, 17D, 17E, and 17F are top, left, right, bottom, rear, and front elevational views, respectively, of the device for cardiac surgery from FIG. 15.

FIGS. 15 and 16 are perspective and top views, respectively, of another embodiment of a device 210 for cardiac surgery. The device 210 has a frame 212 that is a single piece. In other embodiments, however, the frame 212 could be in one or more parts which are movable relative to each other. In this embodiment, the frame has first, second, and third tabs 214A, 214B, 214C which protrude upward from the frame and then arch inward. Suture guides 216A, 216B make up a first pair of suture guides 216. Suture guides 218A, 218B make up a second pair of suture guides 218. Suture guides 220A, 220B make up a third pair of suture guides 220. Each of the first, second, and third pairs of suture guides 216, 218, 220 are located on a respective first, second, and third tab 214A, 214B, 214C of the frame 212. In this embodiment, the suture guides 216A, 216B, 218A, 218B, 220A, 220B are tapered with the guides being more narrow on the bottom side than the top. Also in this embodiment, the tabs 214A, 214B, 214C have each been reinforced with a respective stabilizer 222A, 222B, 222C to help keep the tabs 214A, 214B, 214C from bending. Other embodiments may not have stabilizers. As viewed from the top view of FIG. 16 in this embodiment, the suture guides

216A, 216B, 218A, 218B, 220A, 220B each substantially fall on the same imaginary circle.

FIGS. 17A, 17B, 17C, 17D, 17E, and 17F are top, left, right, bottom, rear, and front elevational views, respectively, of the device 210 for cardiac surgery from FIG. 15.

Figure 18:
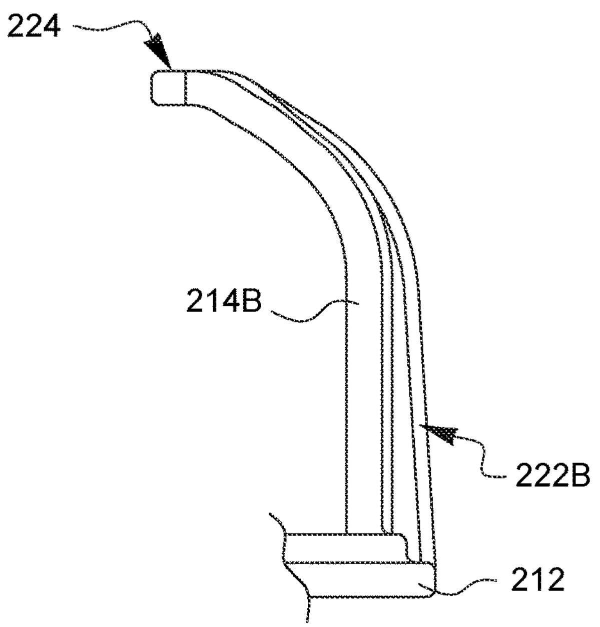
FIG. 18 is a side view of one of the tabs protruding from the frame of the device for cardiac surgery from FIG. 15.

FIG. 18 is a side view of one of the tabs 214B protruding from the frame 212 of the device 210 for cardiac surgery from FIG. 15. In this embodiment, the end 224 of the tab 214B which is away from the frame 212 (and in which the suture guides are formed, but not visible in this view) is substantially parallel to the frame 212.

Figure 19A:
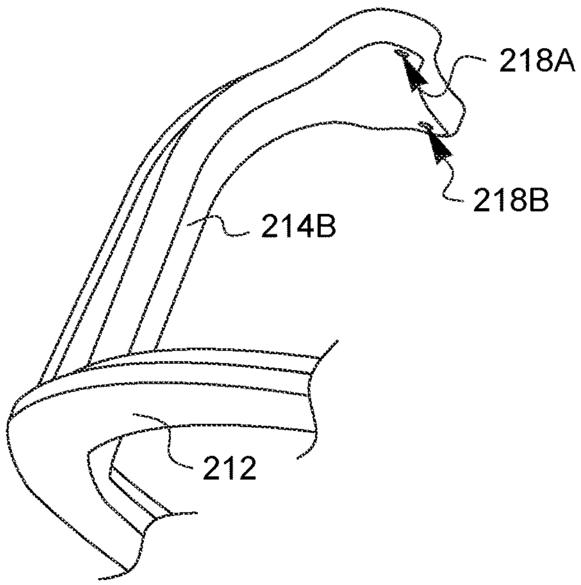
FIGS. 19A and 19B are bottom and top perspective views, respectively of one of the tabs protruding from the frame of the device for cardiac surgery from FIG. 15.
Figure 19B:
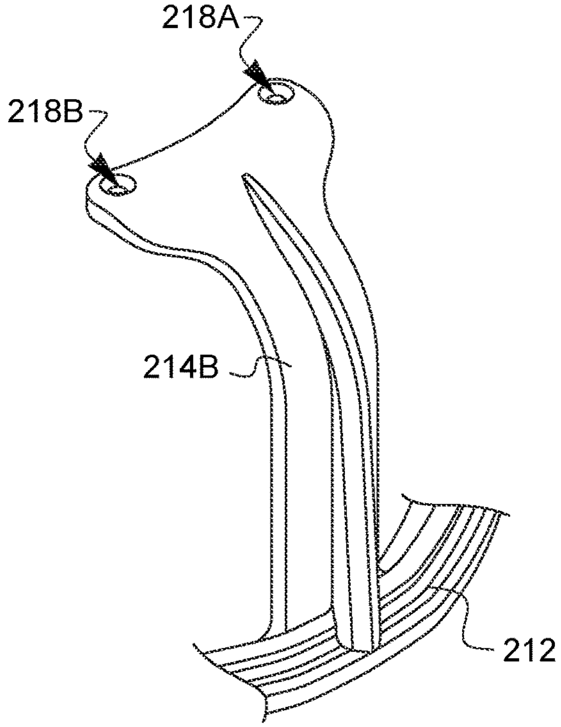
Figure 20A:
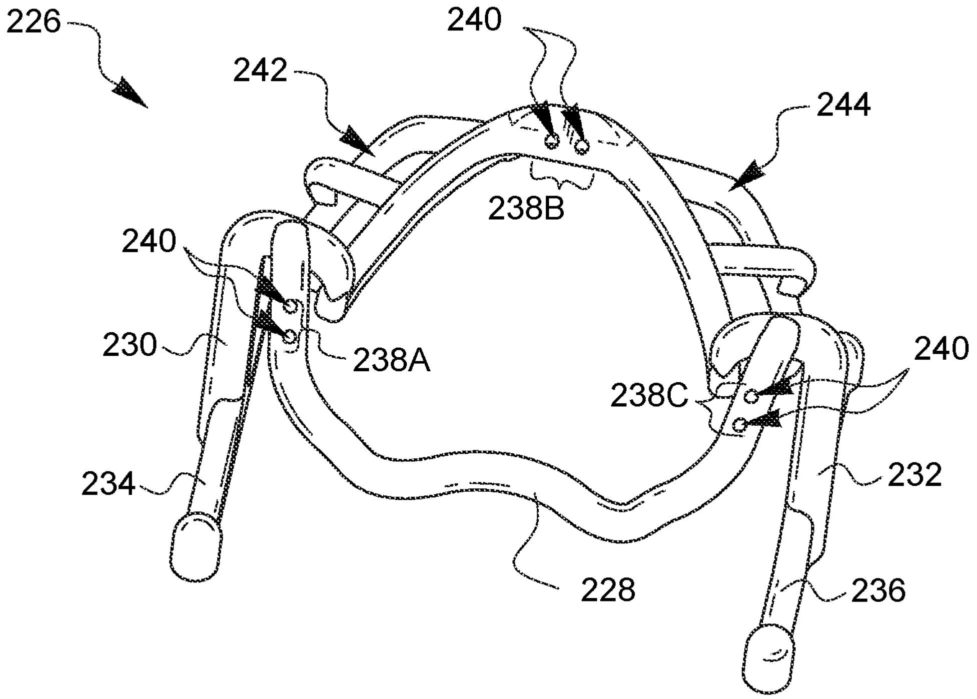
FIGS. 20A-20E are top perspective, top-right perspective, right perspective, right-rear perspective, and rear perspective views, respectively of another embodiment of a device for cardiac surgery.
Figure 20B:
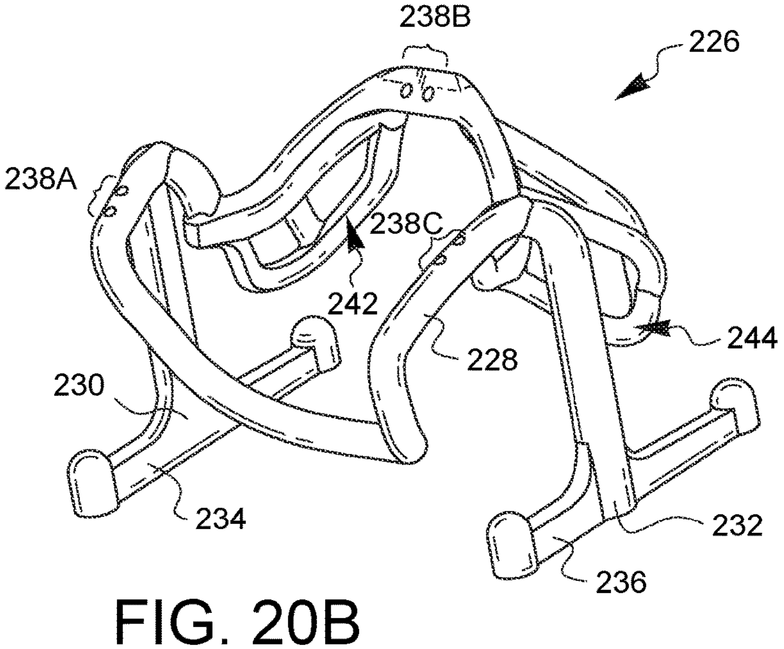
Figure 20C:
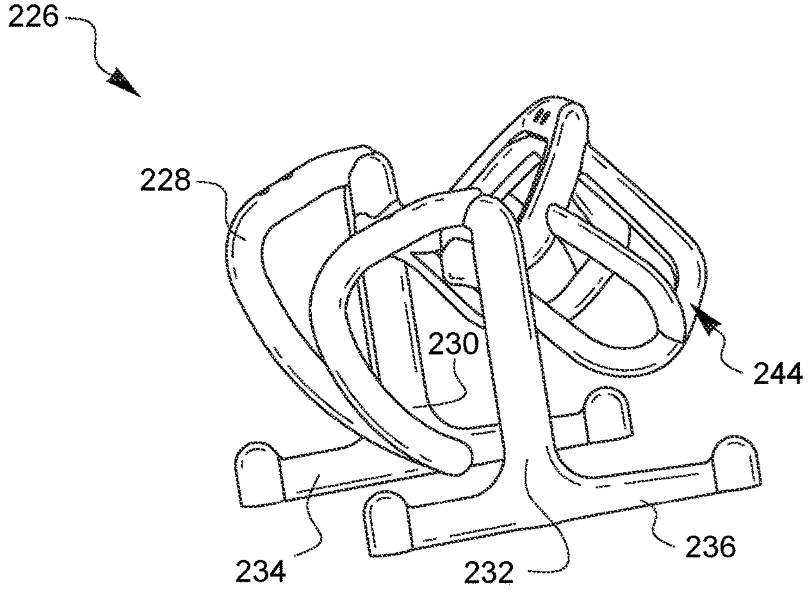
Figure 20D:
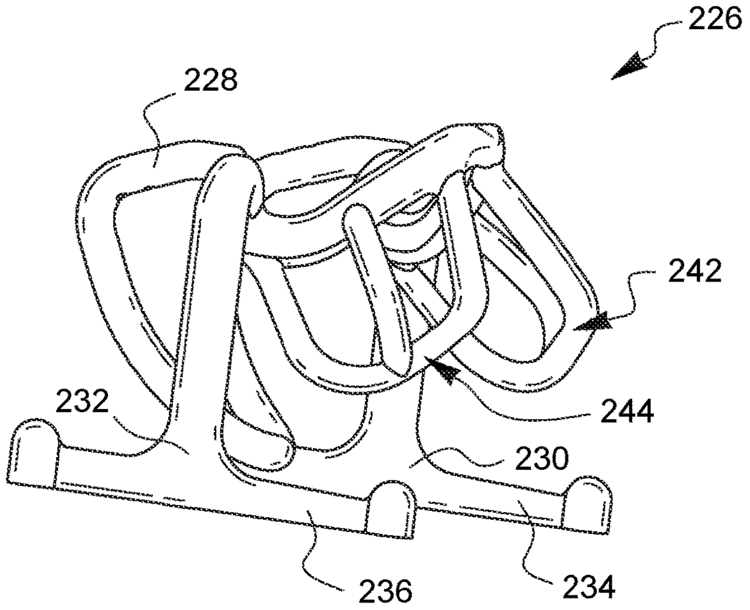
Figure 20E:
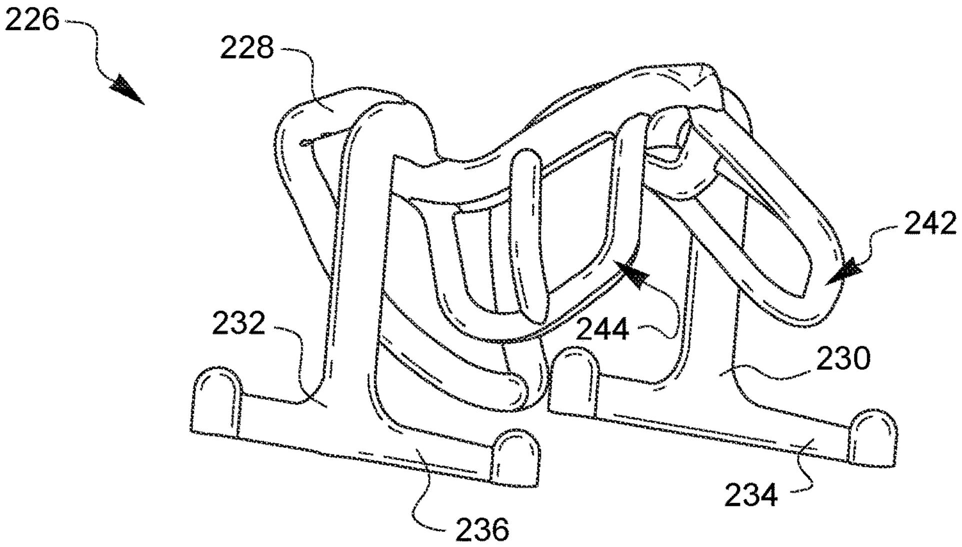
Figure 21A:
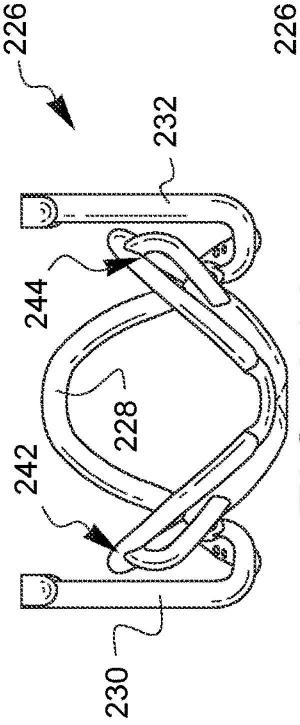
FIGS. 21A, 21B, 21C, 21D, 21E, and 21F are rear, top, left side, right side, bottom, and front elevational views, respectively of the device for cardiac surgery from FIGS. 20A-20E.
Figure 21B:
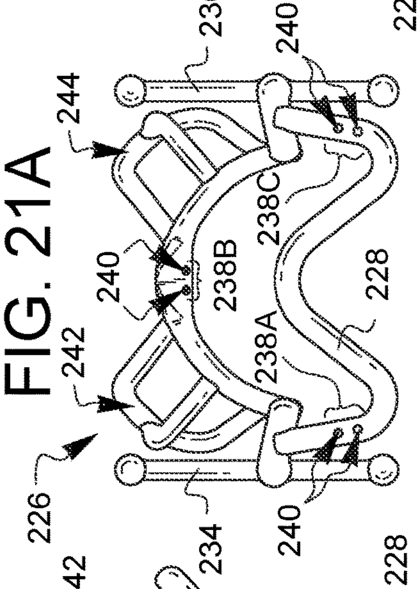
Figure 21C:
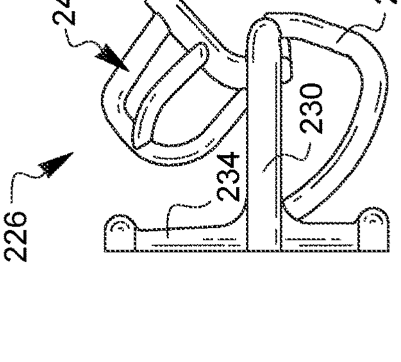
Figure 21D:
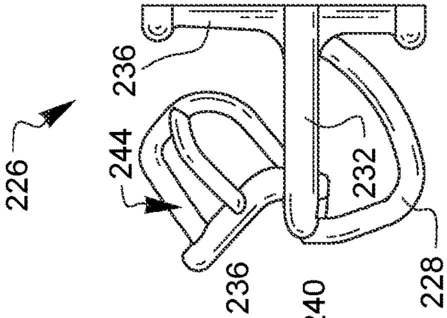
Figure 21E:
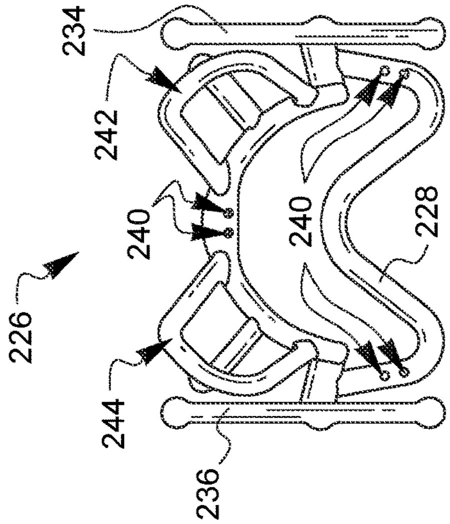
Figure 21F:
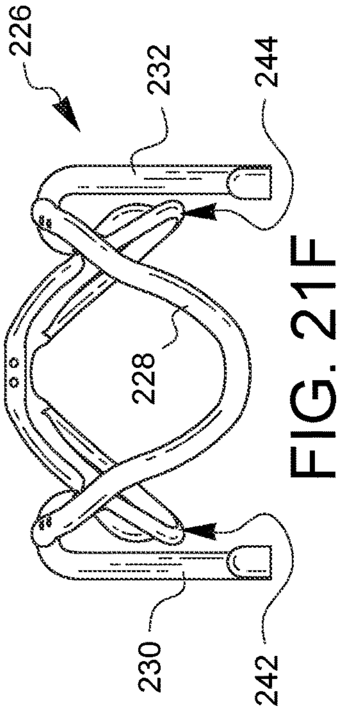

FIGS. 19A and 19B are bottom and top perspective views, respectively of one of the tabs 214B protruding from the frame 212 of the device 210 for cardiac surgery from FIG. 15. FIGS. 19A and 19B offer another vantage point to appreciate the tapered suture guide holes 218A, 218B of this embodiment. Other embodiments may not have tapered guide holes or the suture guide holes may be tapered in a different direction. Still other embodiments may have suture guide holes which are tapered outward (wider) where they exit on both sides of the tab/frame.

FIGS. 20A-20F are top perspective, top-right perspective, right perspective, right-rear perspective, and rear perspective views, respectively of another embodiment of a device 226 for cardiac surgery. The device 226 has a frame 228 from which support legs 230, 232 extend downward. Each support leg 230, 232 terminates in a respective support foot, 234, 236. This embodiment has three pairs 238A, 238B, 238C of suture guides 240 spaced about the frame 228. The suture guides 240 may be used as described for the suture guides of previous embodiments. The device 226 also has two sinus supports 242, 244 which extend outward from the frame 228. The sinus supports 242, 244 are each shaped to support an aortic sinus. An aortic sinus is one of the anatomic dilations of the ascending aorta which occurs just above the aortic valve. There are generally three aortic sinuses, one anterior and two posterior. The left posterior aortic sinus gives rise to the left coronary artery and the anterior artic sinus gives rise to the right coronary artery. During cardiac surgery, it is sometimes desirable to have fluid access to the coronary arteries, for example, to deliver solutions which can stop and start the heart. When an aortotomy is made to gain access to the aortic valve and/or other areas of the heart, the walls of the coronary sinuses may slump down, making it difficult to access the coronary arteries. The sinus supports 242, 244 are sized to fit into the coronary sinuses and hold the coronary sinuses open during a cardiac surgical procedure so that fluids may be administered to the coronary arteries, if desired. Maintaining the shape of the coronary sinuses may also help surgeons to visualize the anatomy of the area in which they are operating. Different devices 226 may be provided with sinus supports 242, 244 of different sizes, to accommodate natural anatomic variations which occur from person to person.

FIGS. 21A, 21B, 21C, 21D, 21E, and 21F are rear, top, left side, right side, bottom, and front elevational views, respectively of the device for cardiac surgery from FIGS. 20A-20E.

Various advantages of a device for cardiac surgery have been discussed above. Embodiments discussed herein have been described by way of example in this specification. It will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. As just one example, although many of the embodiments shown herein included six suture guides, it should be understood that other embodiments may have more or fewer suture guides. As another non-limiting example, the suture guide holes shown in the embodiments herein are fully constrained holes. In other embodiments, the suture guide holes could be in communication with an access channel that would allow a suture to be brought into the suture guide hole by guiding a middle portion of a suture through the access channel and into the suture guide hole. This could avoid the need for a snare to pull the suture through the guide hole in some embodiments. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A device for cardiac surgery, comprising:

a first frame member that extends along a first frame member axis from a first end to a second end, wherein the first frame member axis is non-linear, and wherein a first set of two or more apertures are disposed through the first frame member, each of the first set of two or more apertures configured to receive a corresponding first portion of suture that is configured to secure the first frame member to a first portion of cardiac tissue; and a second frame member that extends along a second frame member axis from a first end to a second end, wherein the second frame member axis is non-linear, and wherein a second set of two or more apertures are disposed through the second frame member, each of the second set of two or more apertures configured to receive a corresponding second portion of suture that is configured to secure the second frame member to a second portion of cardiac tissue, wherein the first end of the first frame member is pivotably coupled to the first end of the second frame member such that the first frame member and the second frame member are pivotably displaceable between a first position and a second position, wherein in the first position, the second end of the first frame member and the second end of the second frame member are separated by a first distance, and in the second position, the second end of the first frame member and the second end of the second frame member are separated by a second distance that is greater than the first distance, and wherein the first frame member is at least partially defined by a first planar top surface that extends from the first end of the first frame member to the second end of the first frame member and a first planar bottom surface that extends from the first end of the first frame member to the second end of the first frame member, and the second frame member is at least partially defined by a second planar top surface that extends from the first end of the second frame member to the second end of the second frame member and a second planar bottom surface that extends from the first end of the second frame member to the second end of the second frame member, and the first top surface and the second top surface are coplanar as the first frame member and the second frame member pivot between the first position and the second position such that the first top surface and the second top surface are coplanar in an intermediate position in which the first frame member and the second frame member are between the first position and the second position, and wherein the first end of the first frame member includes a first contoured edge that defines a recess having a shape of a portion of a first circle having a first diameter, wherein a top end portion of the first contoured edge is at the first planar top surface and a bottom end portion of the first contoured edge is at the first planar bottom surface, and the first end of the second frame member includes a second contoured edge that defines a protrusion having a shape of a portion of a second circle having a second diameter that is equal to or less than the first diameter, wherein a top end portion of the second contoured edge is at the second planar top surface and a bottom end portion of the second contoured edge is at the second planar bottom surface, and wherein the protrusion of the second frame member is disposed within the recess of the first frame member such that the protrusion is rotatable within the recess.

2. The device of claim 1, wherein the second end of the first frame member is not pivotably coupled to the second end of the second frame member.

3. The device of claim 1, wherein the first frame member axis has a shape of a portion of a polygon.

4. The device of claim 1, further comprising a skirt coupled to at least one of the first frame member and the second frame member.

5. The device of claim 1, wherein the first end of the first frame member includes a first hinge portion and the first end of the second frame member includes a second hinge portion, and an elongated pin couples the first hinge portion and the second hinge portion such that the first frame member and the second frame member each rotate about a longitudinal axis of the pin.

6. The device of claim 1, wherein the first frame member axis has a first arcuate shape and the second frame member axis has a second arcuate shape.

7. The device of claim 1, wherein the first frame member and the second frame member pivot about a pivot axis that is normal to the first top surface and the second top surface.

8. The device of claim 1, wherein the first planar bottom surface and the second planar bottom surface are coplanar as the first frame member and the second frame member pivot between the first position and the second position such that the first planar bottom surface and the second planar bottom surface are coplanar in an intermediate position in which the first frame member and the second frame member are between the first position and the second position.

* * * * *